(12) United States Patent  (10) Patent No.: US 8,777,955 B2
Park  (45) Date of Patent: Jul. 15, 2014

(54) ARTHROPLASTY SYSTEMS AND DEVICES, AND RELATED METHODS

(71) Applicant: OtisMed Corporation, Alameda, CA (US)

(72) Inventor: Ilwhan Park, Walnut Creek, CA (US)

(73) Assignee: OtisMed Corporation, Alameda, CA (US)

( * ) Notice: Subject to any disclaimer, the term of this patent is extended or adjusted under 35 U.S.C. 154(b) by 0 days.

(21) Appl. No.: 13/723,904

(22) Filed: Dec. 21, 2012

(65) Prior Publication Data

US 2013/0115474 A1  May 9, 2013

Related U.S. Application Data

(63) Continuation of application No. 11/924,425, filed on Oct. 25, 2007, now Pat. No. 8,460,303.

(51) Int. Cl.
*A61F 5/00* (2006.01)

(52) U.S. Cl.
USPC ............... 606/87; 606/86 R; 606/89; 409/219

(58) Field of Classification Search
USPC .......... 606/86 R–89 R, 293; 409/2, 3, 79, 80, 409/282, 291, 292, 903, 6, 7, 175, 219, 224, 409/227
See application file for complete search history.

(56) References Cited

U.S. PATENT DOCUMENTS

| | | | |
|---|---|---|---|
| 4,517,969 A | 5/1985 | Halcomb et al. | |
| 5,098,436 A | 3/1992 | Ferrante et al. | |
| 5,298,254 A | 3/1994 | Prewett et al. | |
| 5,916,221 A | 6/1999 | Hodorek et al. | |
| 6,799,066 B2 | 9/2004 | Steines et al. | |
| 7,715,602 B2 | 5/2010 | Richard | |
| 8,052,623 B2 | 11/2011 | Haimerl et al. | |
| 8,115,485 B1 | 2/2012 | Maier et al. | |
| 8,165,657 B2 | 4/2012 | Krueger | |
| 8,170,716 B2 | 5/2012 | Coste-Maniere et al. | |
| 8,224,127 B2 | 7/2012 | Woodard et al. | |
| 8,460,302 B2 | 6/2013 | Park et al. | |
| 8,460,303 B2 | 6/2013 | Park | |

(Continued)

FOREIGN PATENT DOCUMENTS

| | | |
|---|---|---|
| JP | 10-94538 | 4/1998 |
| JP | 2001-092950 | 4/2001 |
| WO | WO 00/35346 | 6/2000 |

OTHER PUBLICATIONS

Amendment Under 37 C.F.R. 1.312, U.S. Appl. No. 13/374,960, filed May 7, 2013, 6 pages.

(Continued)

*Primary Examiner* — Andrew Yang
(74) *Attorney, Agent, or Firm* — Polsinelli PC

(57) ABSTRACT

Systems for manufacturing arthroplasty jigs are disclosed. The systems include positioning components for positioning an arthroplasty jig blank in a machining device (e.g., a computer numerical control (CNC) machine). Arthroplasty jig blanks that may be used in the systems can include an arm fixture component configured to be coupled to the positioning component. Coupling the arm fixture component to the positioning component positions the jig blank body for machining by the machining device. In addition, positioning components, arthroplasty jig blanks, and methods for making arthroplasty jig blanks are disclosed.

20 Claims, 18 Drawing Sheets

(56) References Cited

U.S. PATENT DOCUMENTS

| | | | |
|---|---|---|---|
| 8,480,679 | B2 | 7/2013 | Park |
| 8,483,469 | B2 | 7/2013 | Pavlovskaia et al. |
| D691,719 | S | 10/2013 | Park |
| 8,545,509 | B2 | 10/2013 | Park et al. |
| 2004/0146369 | A1* | 7/2004 | Kato ............................ 409/219 |
| 2005/0054914 | A1 | 3/2005 | Duerk et al. |
| 2005/0272998 | A1 | 12/2005 | Diehl et al. |
| 2006/0079755 | A1 | 4/2006 | Stazzone et al. |
| 2006/0244448 | A1 | 11/2006 | Ballon et al. |
| 2007/0010732 | A1 | 1/2007 | DeYoe et al. |
| 2007/0100338 | A1 | 5/2007 | Deffenbaugh et al. |
| 2007/0123856 | A1 | 5/2007 | Deffenbaugh et al. |
| 2007/0123857 | A1 | 5/2007 | Deffenbaugh et al. |
| 2008/0089591 | A1 | 4/2008 | Zhou et al. |
| 2009/0085567 | A1 | 4/2009 | Kimmlingen et al. |
| 2011/0071537 | A1 | 3/2011 | Koga et al. |
| 2013/0116697 | A1 | 5/2013 | Park et al. |
| 2013/0123789 | A1 | 5/2013 | Park |
| 2013/0190767 | A1 | 7/2013 | Park et al. |

OTHER PUBLICATIONS

Final Office Action, U.S. Appl. No. 12/636,939, mailed Jan. 25, 2013, 9 pages.
Final Office Action, U.S. Appl. No. 12/546,545, dated Oct. 7, 2013, 24 pages.
Non-Final Office Action, U.S. Appl. No. 11/641,569, mailed Jul. 12, 2013, 21 pages.
Non-Final Office Action, U.S. Appl. No. 11/642,385, dated Oct. 22, 2013, 37 pages.
Non-Final Office Action, U.S. Appl. No. 11/656,323, dated Oct. 22, 2013, 36 pages.
Non-Final Office Action, U.S. Appl. No. 11/946,002, dated Oct. 2, 2013, 39 pages.
Non-Final Office Action, U.S. Appl. No. 12/390,667, mailed May 8, 2013, 20 pages.
Non-Final Office Action, U.S. Appl. No. 12/505,056, mailed Jun. 28, 2013, 7 pages.
Non-Final Office Action, U.S. Appl. No. 12/636,939, mailed Apr. 25, 2013, 16 pages.
Non-Final Office Action, U.S. Appl. No. 12/760,388, mailed Jun. 20, 2013, 54 pages.
Non-Final Office Action, U.S. Appl. No. 13/730,585, mailed Jun. 11, 2013, 10 pages.
Non-Final Office Action, U.S. Appl. No. 13/730,608, dated Oct. 7, 2013, 10 pages.
Notice of Allowance, Design U.S. Appl. No. 29/394,882, mailed May 24, 2013, 16 pages.
Notice of Allowance, U.S. Appl. No. 12/563,809, mailed May 28, 2013, 11 pages.
Notice of Allowance, U.S. Appl. No. 13/086,275, mailed Aug. 27, 2013, 31 pages.
Notice of Allowance, U.S. Appl. No. 13/374,960, mailed May 6, 2013, 20 pages.
Preliminary Amendment, U.S. Appl. No. 13/731,697, filed May 10, 2013, 6 pages.
Response to Final Office Action, U.S. Appl. No. 12/563,809, filed May 6, 2013, 15 pages.
Response to Non-Final Office Action, U.S. Appl. No. 13/086,275, filed May 7, 2013, 11 pages.
Response to Non-Final Office Action, U.S. Appl. No. 12/546,545, filed Jul. 15, 2013, 14 pages.
Response to Non-Final Office Action, U.S. Appl. No. 12/636,939, filed Jul. 16, 2013, 15 pages.
Response to Non-Final Office Action, U.S. Appl. No. 12/390,667, filed Aug. 7, 2013, 22 pages.
Response to Non-Final Office Action, U.S. Appl. No. 12/760,388, filed Sep. 12, 2013, 15 pages.
Response to Non-Final Office Action, U.S. Appl. No. 12/505,056, filed Oct. 9, 2013, 17 pages.
Response to Non-Final Office Action, U.S. Appl. No. 13/730,585, filed Oct. 9, 2013, 15 pages.
Response to Non-Final Office Action, U.S. Appl. No. 11/641,569, filed Oct. 11, 2013, 12 pages.
U.S. Appl. No. 13/749,095, filed Jan. 24, 2013, Song.
U.S. Appl. No. 13/923,093, filed Jun. 20, 2013, Park.
U.S. Appl. No. 13/960,498, filed Aug. 6, 2013, Song.
U.S. Appl. No. 14/011,998, filed Aug. 28, 2013, Park et al.
U.S. Appl. No. 14/084,255, filed Nov. 19, 2013, Park et al.
U.S. Appl. No. 14/086,849, filed Nov. 21, 2013, Park et al.
U.S. Appl. No. 14/086,878, filed Nov. 21, 2013, Park et al.
Final Office Action, U.S. Appl. No. 11/641,569, dated Nov. 29, 2013, 20 pages.
Final Office Action, U.S. Appl. No. 12/505,056, dated Dec. 30, 2013, 48 pages.
Final Office Action, U.S. Appl. No. 13/730,585, dated Dec. 27, 2013, 8 pages.
Japanese Office Action, JP Application No. 2011-507530, dated Dec. 17, 2013, 8 pages.
Non-Final Office Action, U.S. Appl. No. 11/946,002, dated Feb. 6, 2014, 46 pages.
Non-Final Office Action, U.S. Appl. No. 13/730,467, dated Jan. 15, 2014, 8 pages.
Notice of Allowance, U.S. Appl. No. 11/641,569, dated Feb. 5, 2014, 11 pages.
Notice of Allowance, U.S. Appl. No. 12/390,667, dated Jan. 17, 2014, 9 pages.
Notice of Allowance, U.S. Appl. No. 12/546,545, dated Dec. 26, 2013, 9 pages.
Notice of Allowance, U.S. Appl. No. 12/760,388, dated Jan. 22, 2014, 13 pages.
Response to Final Office Action, U.S. Appl. No. 11/641,569, dated Jan. 29, 2014, 10 pages.
Response to Final Office Action, U.S. Appl. No. 12/390,667, dated Dec. 23, 2013, 5 pages.
Response to Final Office Action, U.S. Appl. No. 12/546,545, dated Dec. 9, 2013, 8 pages.
Response to Non-Final Office Action, U.S. Appl. No. 11/946,002, filed Dec. 6, 2013, 18 pages.
Response to Non-Final Office Action, U.S. Appl. No. 13/730,608, dated Jan. 7, 2014, 16 pages.
Response to Non-Final Office Action, U.S. Appl. No. 11/656,323, dated Jan. 17, 2014, 10 pages.
Siemens MAGNETOM Sonata 1.5T Technical Specifications, pp. 1-4, accessed online Jan. 28, 2014.

* cited by examiner

ARTHROPLASTY SYSTEMS AND DEVICES, AND RELATED METHODS

CROSS-REFERENCE TO RELATED APPLICATIONS

The present application is a continuation application of U.S. application Ser. No. 11/924,425 filed Oct. 25, 2007. The '425 application is incorporated by reference herein for all that it discloses or teaches.

This application is also related to U.S. Design patent application No. 29/296,687 filed Oct. 25, 2007 entitled "Arthroplasty Jig Blank," and now U.S. Design Pat. No. D642,263 dated Jul. 26, 2011. The '687 application is incorporated by reference in its entirety.

TECHNICAL FIELD

Described here are systems, devices, and methods for use in the field of arthroplasty. More specifically, described here are arthroplasty jig blanks and systems and methods that may be used to make arthroplasty jigs, such as custom arthroplasty jigs, from the arthroplasty jig blanks.

BACKGROUND

Arthroplasty is commonly used to repair and replace joints damaged from wear, injury, and/or disease. Common arthroplasty procedures can include joint remodel or repair, or implantation of an artificial joint or joint component or implant. Arthroplasty procedures can be used to repair many different joints and joint-like areas in the body, such as the knee, hip, elbow, shoulder, or spine.

The success of an arthroplasty procedure can often be correlated to the degree of fit between the artificial joint or joint components and the patient's surrounding body structures. That is, improving the fit between an artificial joint component and the surrounding bones, cartilage, and musculature may reduce stress on the affected joint and associated structures. This, in turn, may reduce the likelihood of the patient requiring subsequent joint repair, and may also reduce overall complications experienced by the patient during and/or after the arthroplasty procedure.

In an arthroplasty procedure involving the use of an implant to repair a damaged joint, the damaged joint may be prepared for the implant prior to implantation. For example, in a knee arthroplasty procedure, the femur and/or tibia may be treated (e.g., cut, drilled, reamed and/or resurfaced) to provide one or more surfaces that are configured to receive the implant. Certain surgical tools, such as arthroplasty jigs, may be used to accurately position and/or control one or more of the instruments that are used to provide such treatment, such as saws, drills, reamers, and the like. Arthroplasty jigs may be configured with apertures or slots to control the position, length, and/or depth of the instruments. Moreover, enhanced accuracy and precision may be provided in an arthroplasty procedure by using custom or patient-specific arthroplasty jigs. Such arthroplasty jigs are configured for use in certain anatomical target sites of a particular patient. Examples of arthroplasty jigs, including custom arthroplasty jigs, are disclosed in U.S. patent application Ser. No. 11/641,569, filed Dec. 18, 2006, U.S. patent application Ser. No. 11/642,385, filed Dec. 19, 2006, and U.S. patent application Ser. No. 11/656,323, filed Jan. 19, 2007, each of which is hereby incorporated by reference in its entirety.

It would be desirable to provide methods and/or tools for making arthroplasty jigs, including custom or patient-specific arthroplasty jigs, relatively efficiently. For example, it would be desirable to provide methods that reduce the time and/or cost associated with the fabrication of arthroplasty jigs. It would also be desirable to provide methods that result in enhanced accuracy and precision in the manufacturing of arthroplasty jigs, such as custom arthroplasty jigs.

SUMMARY

Described here are systems and methods that may be used to form arthroplasty jigs from arthroplasty jig blanks. These systems and methods may allow arthroplasty jigs to be manufactured relatively efficiently and/or cost-effectively. Additionally, these systems and methods may provide enhanced positioning and/or stabilization of an arthroplasty jig blank during a machining procedure. This, in turn, may result in the relatively accurate formation of a desired arthroplasty jig. For example, the improved stabilization and positioning of a jig blank during machining may allow for accurate machining of detailed features on a surface of the jig blank, especially features having relatively small dimensions. Thus, by using the systems, methods, and jig blanks described here, the resulting arthroplasty jigs may exhibit improved feature resolution and/or customization. Further, the systems, methods and jig blanks may improve machining accuracy even while decreasing machining time, thereby producing arthroplasty jigs with improved fit and reduced cost.

Some variations of arthroplasty jig manufacturing systems described here comprise a first positioning component and an arm fixture component. The arm fixture component is integral with, or configured to be coupled to, an arthroplasty jig blank body. The first positioning component is integral with, or configured to be coupled to, a machining device, such as a computer numerical control (CNC) machine. Further, the arm fixture component is configured to couple to the first positioning component so that the jig blank body can be positioned for machining by the machining device.

In certain variations, the first positioning component may be configured to position the jig blank body along a plane defined by two translational axes of the machining device when the arm fixture component is coupled to the first positioning component. The arm fixture component may include a first surface and a second surface. When the arm fixture component is coupled to the first positioning component, the first surface may be aligned with one of the translational axes of the machining device, and the second surface may be aligned with another translational axis of the machining device. The translational axes of the machining device may be, for example, X- and Y-axes that define a plane (e.g., a horizontal plane).

In some variations, the first positioning component may be configured to rotate the jig blank around a rotational axis of the machining device when the arm fixture component is coupled to the first positioning component. In certain variations, the arm fixture component may be coupled to the first positioning component, and the first positioning component may position the jig blank body so that a volume of the jig blank body is accessible by one or more machining tools of the machining device. In some systems, a volume of the jig blank body that is at least about 30 cubic inches, or at least about 40 cubic inches, may be accessible by one or more machining tools as the jig blank body is positioned via the arm fixture component coupled to the first positioning component. The arm fixture component may have a dimension of, for example, about 4 inches to about 8 inches.

The arm fixture component may have any suitable shape or configuration. The arm fixture component shape and/or configuration may be selected to provide accurate alignment and mounting of the jig blank body in the positioning component, and/or to maintain the position of the jig blank body even while it is under force and/or torque from machining tools. In some variations, the arm fixture component may comprise a U-shaped member configured to couple to the first positioning component. Certain variations of the systems may include a clamp, one or more screws, a lock, or the like, configured to releasably secure the arm fixture component to the first positioning component.

Variations of the arthroplasty jig manufacturing systems may include a second positioning component. As with the first positioning component, the second positioning component may be integral with, or configured to be coupled to, a machining device, such as a CNC machine. In these systems, the arm fixture component may be configured to be coupled to both the first positioning component and the second positioning component. When the arm fixture component is coupled to both the first and second positioning components, the jig blank body may be positioned for machining by the machining device (e.g., a CNC machine). Here, the arm fixture component may comprise first and second U-shaped members. The first U-shaped member may be configured to couple to the first positioning component, and the second U-shaped member may be configured to couple to the second positioning component. Variations of these systems may include a clamp, one or more screws, a lock, or the like, configured to releasably secure the arm fixture component to the second positioning component.

The arthroplasty jig manufacturing systems described here may be adapted for any suitable application. For example, the systems may be used to manufacture knee, hip, shoulder, elbow, and/or spinal arthroplasty jigs. Correspondingly, the arthroplasty jig blanks used in the systems may comprise knee arthroplasty jig blanks, hip arthroplasty jig blanks, shoulder arthroplasty jig blanks, elbow arthroplasty jig blanks, or spinal arthroplasty jig blanks. In some variations, the arthroplasty jig blanks may be suitable for use in forming multiple different types of arthroplasty jigs. For example, a single arthroplasty jig blank may be used to form either a knee arthroplasty jig or a hip arthroplasty jig.

Also described here are positioning components for positioning a jig blank body of an arthroplasty jig blank in a machining device, such as a CNC machine. The positioning components include a positioning component body that is integral with, or configured to be coupled to, the machining device. The positioning component body comprises a first registration portion that is configured to couple with the arthroplasty jig blank. Coupling the first registration portion with the arthroplasty jig blank positions the jig blank body along or about one or more axes of the machining device to allow for machining of at least a portion of the jig blank body. In certain variations, the positioning component body may be configured to rotate about a first rotational axis of the machining device.

In some variations of the positioning components, the first registration portion is configured to be aligned with a first translational axis of the machining device, and to slidably engage an arm fixture component of the arthroplasty jig blank. Variations of positioning components may comprise a second registration portion configured to be aligned with a second translational axis of the machining device. The second registration portion may abut the arm fixture component when the first registration portion slidably engages the arm fixture component.

Methods for machining arthroplasty jigs are also described. The methods include coupling an arm fixture component of an arthroplasty jig blank to a first positioning component that is coupled to, or integral with, a machining device (e.g., a CNC machine). The first positioning component is adjusted to position a jig blank body of the arthroplasty jig blank along or about one or more axes of the machining device. The methods include machining at least a portion of the jig blank body with one or more machining tools of the machining device to form the arthroplasty jig. Some variations of the methods may include coupling the arm fixture component of the arthroplasty jig blank to a second positioning component that is coupled to, or integral with, the machining device.

In certain methods, the first positioning component is adjusted to position the jig blank body by rotating the first positioning component about a rotational axis of the machining device. In some variations, the first positioning component may be rotated a full 360° about a rotational axis of the machining device. Adjusting the first positioning component to position the jig blank body may comprise translating the first positioning component along one or more translational axes (e.g., an X-axis and/or a Y-axis) that may define a plane (e.g., a horizontal plane).

Further, arthroplasty jig blanks are described herein. The arthroplasty jig blanks include a jig blank body and an arm fixture component that is integral with, or coupled to, the jig blank body. In the arthroplasty jig blanks, the arm fixture component is configured to be coupled to a machining device (e.g., a CNC machine) to position the jig blank body so that at least a portion of the jig blank body can be machined by the machining device. For example, the jig blank body may be rotated about or translated along one or more axes of the machining device to allow machining of at least a portion of the jig blank body. In some variations of the jig blanks, the arm fixture component may be configured to be slidably coupled to a positioning component that, in turn, is coupled to, or integral with, the machining device.

Methods of making an arthroplasty jig blank also are described. These methods include forming a mold, filling the mold with a moldable polymer, curing or setting the polymer in the mold, and releasing the mold to form an arthroplasty jig blank. The arthroplasty jig blank comprises a jig blank body and an arm fixture component integral with, or coupled to, the jig blank body. Any suitable polymer molding technique may be used including, for example, injection molding and/or compression molding. The arm fixture component may be configured to couple to a machining device to allow machining of at least a portion of the jig blank body.

BRIEF DESCRIPTIONS OF THE DRAWINGS

Figure 10:
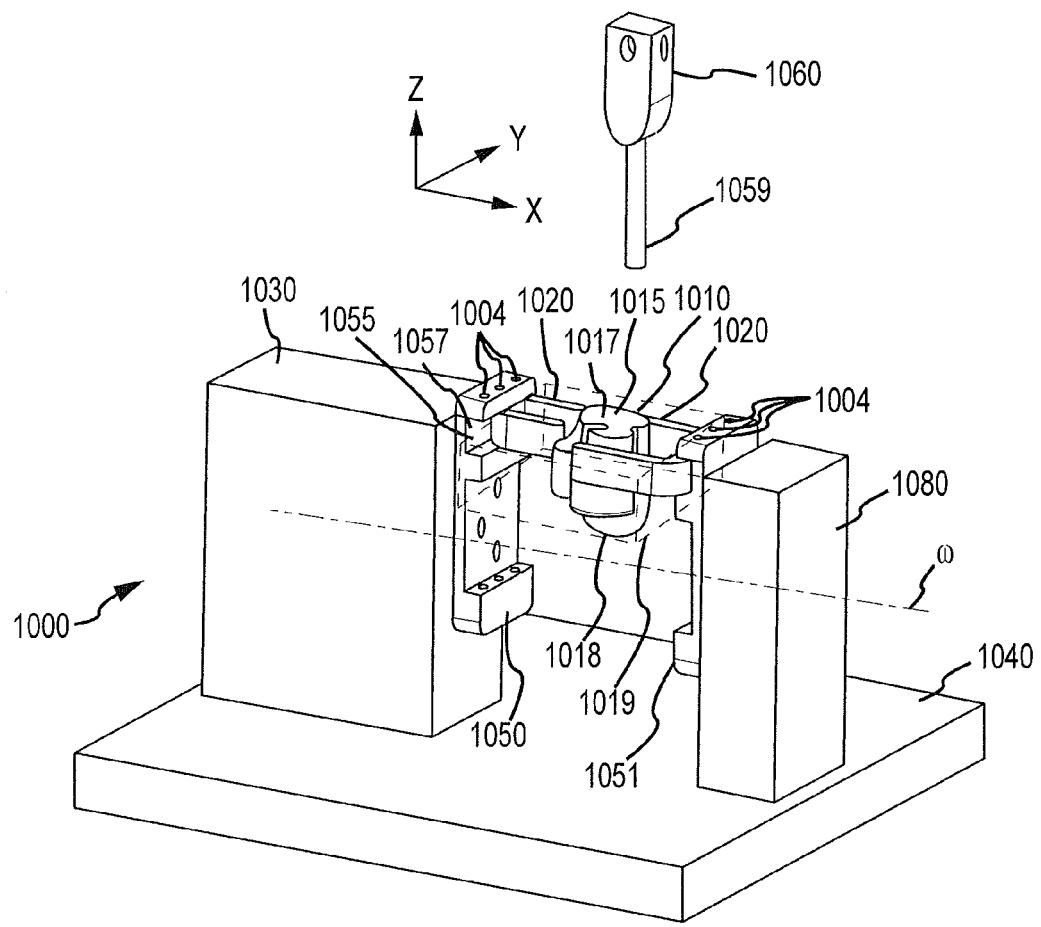

FIG. 10 schematically illustrates a variation of a method of machining an arthroplasty jig blank to form an arthroplasty jig.

Figure 11A:
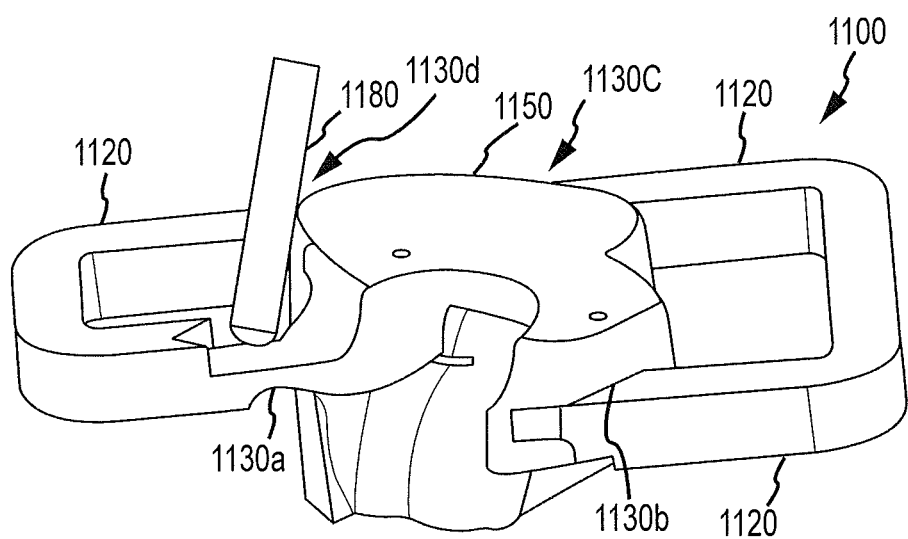
Figure 11B:
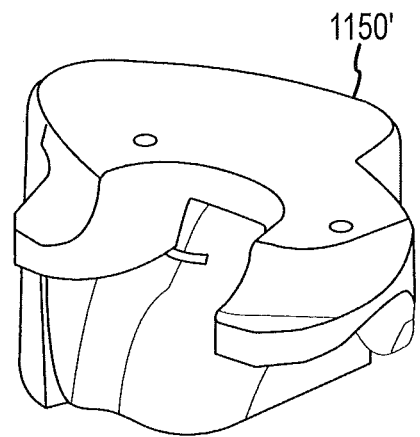

FIGS. 11A and 11B illustrate an example of a machining step to remove an arm fixture component from a machined arthroplasty jig blank to form an arthroplasty jig.

Figure 12:
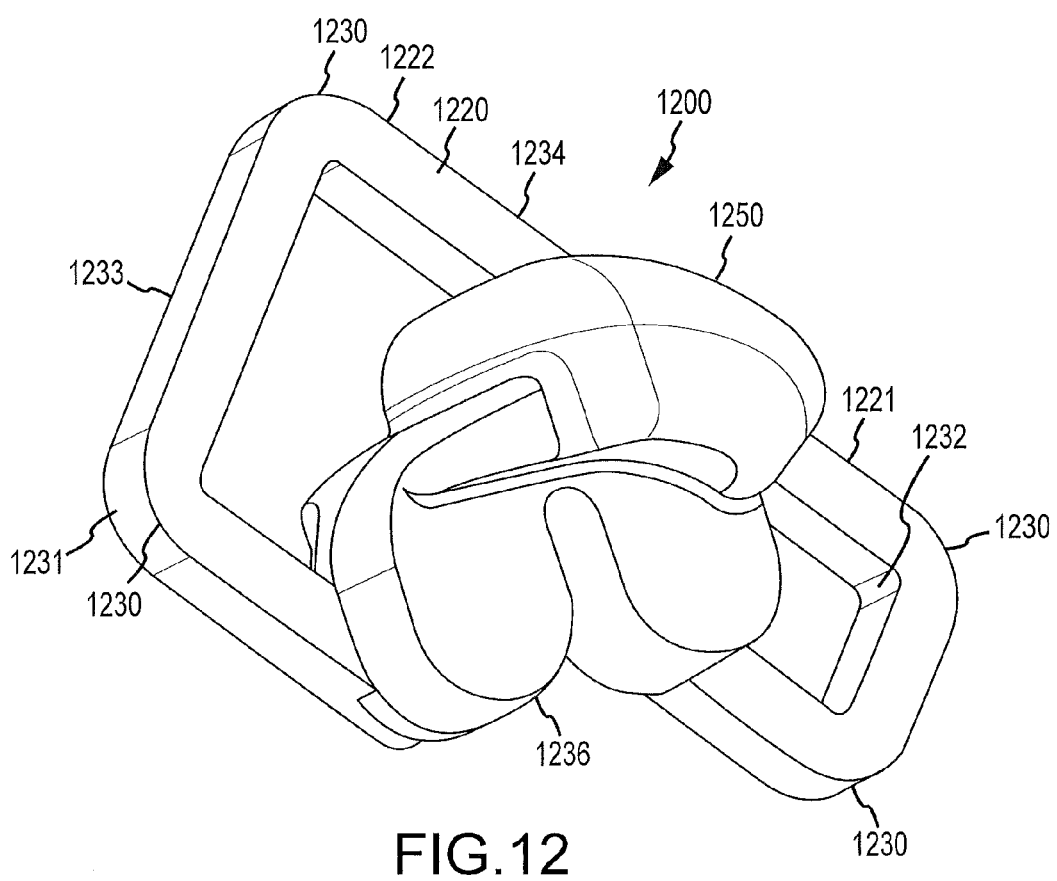

FIG. 12 is a perspective view of a variation of an arthroplasty jig blank.

DETAILED DESCRIPTIONS

Described here are systems, methods, arthroplasty jig blanks, and positioning components that can be used in the manufacture of arthroplasty jigs. Non-limiting examples of such arthroplasty jigs include knee arthroplasty jigs, which can be adapted for the tibia and/or the femur, hip arthroplasty jigs, elbow arthroplasty jigs, and spinal arthroplasty jigs. Further, methods for making arthroplasty jig blanks are described.

The methods, systems, and positioning components described here, as well as the arthroplasty jig blank configurations described here, may provide relatively stable mounting of the arthroplasty jig blanks into a machining device. The mounting can allow for rotation and translation of the jig blanks to provide ample machine tool access to the jig blank bodies. In addition, the mounting may provide sufficient stability to secure the positions of the jig blanks, even in the presence of force (e.g., vertical force) and/or torque (rotational force) from the machining process. The relatively stable mounting and positioning may, in turn, allow for relatively accurate machining, even of detailed features, on the jig blank bodies. In addition, all or part of the machining device's coordinate system may be transferred to the jig blank bodies, so that machine files written in the machining device's reference frame may be applied directly to the jig blanks (e.g., without a need for axis conversion or for verification of the jig blanks' positions relative to the machining device). When used with an automated machining device, such as a CNC machine, the systems and methods may provide for the relatively rapid and/or accurate manufacturing of arthroplasty jigs, such as custom arthroplasty jigs. Decreased manufacturing time resulting from the use of the systems and methods described here may lower manufacturing costs, even while the machined arthroplasty jigs exhibit equivalent or improved accuracy in comparison to arthroplasty jigs manufactured using other systems and methods.

As described above, in some variations, custom arthroplasty jigs may be formed. Before fabrication of a custom arthroplasty jig to be used in an arthroplasty procedure for a particular subject (e.g., a patient), the affected joint may be mapped out preoperatively. Imaging techniques, such as computed tomography (CT) or magnetic resonance imaging (MRI), may be used to obtain a series of two-dimensional images to map out the affected region. For knee arthroplasty, the affected region may include the lower (distal) end of the femur and/or the upper (proximal) end of the tibia. The series of two-dimensional images can be used to create a three-dimensional model of the damaged bone region. For example, the three-dimensional model may be created by using the two-dimensional images to determine location coordinate values of each of a sequence of spaced apart surface points along the damaged bone surface. A mathematical computer model may then be used to generate the three-dimensional model. Examples of mathematical computer models that can be used to generate three-dimensional models include Analyze (from AnalyzeDirect, Inc., Overland Park, Kans.), Insight Toolkit (open-source software available from the National Library of Medicine Insight Segmentation and Registration Toolkit (ITK), www.itk.org), and 3D Slicer (open-source software available from www.slicer.org). Other appropriate mathematical computer models may also be used.

After the computer-generated three-dimensional model has been formed, it may be used to generate a machine code or set of instructions for input into a computer numerical control (CNC) machine. The machine code can provide instructions to the CNC machine for selective removal of material from an arthroplasty jig blank to shape and fabricate an arthroplasty jig. Because images of the subject's unique bone structure have been used to generate the machine code, custom arthroplasty jigs may be manufactured.

However, mounting and securing a blank, such as an arthroplasty jig blank, in a machining device such as a CNC machine is important to ensure accuracy, especially for the machining of detailed features having small dimensions (e.g., less than about 2 mm, or less than about 1 mm, or less than about 0.5 mm, or even smaller). In addition, because custom arthroplasty jigs may have complex geometries and/or surface configurations, accessing a workable volume of the jig blank for cutting, milling, drilling and the like without compromising stability or positional accuracy can be difficult. The systems, methods, and jig blanks described here may provide secure mounting in a machining device. They may provide for preservation and transfer of one or more axes of the machining device's coordinate system to the jig blank. As a result, machining instructions provided in the machining device's frame of reference may not need to be transposed into a different set of coordinates, and the position of the jig blank relative to the machining device may not need to be ascertained or verified. That is, a machine code instruction to remove material from the jig blank at a certain location in a specified direction may be provided directly in the machining device's coordinate system. This may simplify the process of generating machining instructions, and also may reduce the likelihood of errors occurring when transposing instructions from one coordinate system to another. It should be pointed out that the methods, systems, positioning components, and arthroplasty jig blanks described here are suitable for use in the manufacture of non-custom arthroplasty jigs (such as arthroplasty jigs that may be used for a variety of different subjects), as well as custom arthroplasty jig blanks (such as arthroplasty jigs that are designed for use for a specific subject).

While a CNC machine is described here, any suitable machining device can be used to form an arthroplasty jig, including an automated machine (e.g., a robotically-operated machine), or a manually-operated machine. CNC machines are available in a variety of configurations, including, for example, CNC drills, CNC milling machines, CNC lathes, CNC saws, and any combination of these machines and/or other machines. An example of a CNC machine that may be used with the systems, methods, and jig blanks described here is a Roland MDX milling machine (e.g., a Roland MDX 650 milling machine or a Roland MDX 540 milling machine).

Figure 1A:
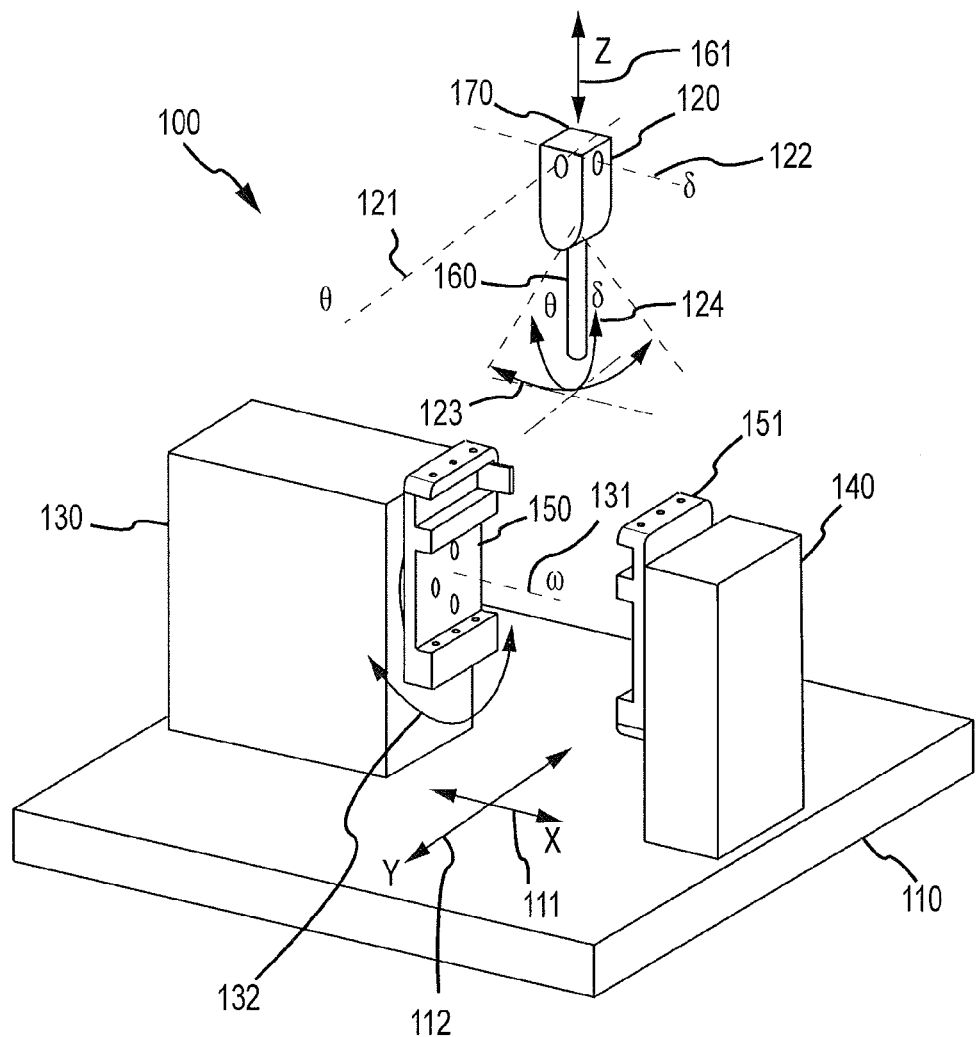
FIG. 1A is a perspective view of a variation of a machining device and two arthroplasty jig blank positioning components.

FIG. 1A illustrates an example of a CNC machine that may be used to form an arthroplasty jig. The CNC machine may machine an arthroplasty jig blank by milling, drilling, cutting, reaming, and/or resurfacing, from multiple angles and sides, according to instructions input into the machine. The CNC machine (100) illustrated in FIG. 1A includes six axes: three translational axes and three rotational axes. However, while CNC machine (100) includes six axes, machining devices with any number of axes (e.g., one, two, three, four, or five, or more than six) may be used. The translational axes for CNC machine (100) are shown as X-axis (111), Y-axis (112), and Z-axis (161). The X-axis and the Y-axis define an X-Y plane. A spindle unit (120) includes a cutting tool (160) and can be translated along Z-axis (161), which is perpendicular to the X-Y plane, as well as along X-axis (111) and along Y-axis (112). The X-Y plane defined by the X- and Y-axes may be generally horizontal, and the Z-axis may be in a generally vertical direction perpendicular to the X-Y plane.

Still referring to FIG. 1A, the first rotational axis ω (131) of CNC machine (100) traces out a rotational path indicated by a double-headed arrow (132). In this example, full 360° rotation around first rotational axis ω (131) is possible. The second rotational axis θ (121) traces out a rotational path shown by a double-headed arrow (123), defining a plane. The third rotational axis δ (122) traces out a path indicated by a double-headed arrow (124), defining a plane perpendicular to that defined by rotation about second rotational axis θ (121). The bottom portion (160) of spindle unit (120) can rotate, and represents a cutting member that can comprise varying sizes of interchangeable machining tools (e.g., drill bits, milling tools, reamers, polishers, and the like). Thus, translational motion of the machining tools in the X-direction, Y-direction, or Z-direction can be accomplished by translating spindle unit (120) in the X-direction, Y-direction, or Z-direction. Alternatively, or in addition, an object to be machined can be translated relative to the machining tool by mounting the object on a movable stage, such as an X-Y stage or an X-Y-Z stage (not shown) provided on or as part of table (110). Rotational motion (e.g., by 360°) about first rotational axis ω (131) is enabled by one or more gears or rotatable shafts coupled to a motor or actuator (not shown) in rotary driver (130). Rotational motion about second rotational axis θ (121) and third rotational axis δ (122) is enabled by one or more gears or rotatable shafts coupled to a motor or actuator coupled to spindle unit (120). As an example, some machines may be capable of 180° rotation or even more about third rotational axis δ (122) or second rotational axis θ (121).

Translational and rotational movement along or about each of the above-described axes may be accomplished by any suitable type of motor or actuator. Non-limiting examples of motors and actuators include electric or electromechanical motors such as stepper motors, servo motors, DC motors, AC motors, and the like, linear, rotary, or semi-rotary actuators (e.g., pneumatic actuators, hydraulic actuators, piezoelectric actuators), and combinations of motors and actuators. For example, a rotary driver unit (130) mounted on a table (110) can include a servo motor to drive rotation about first rotational axis ω (131). Spindle unit (120) can be translated in the X-, Y-, and/or Z-directions, for example, using stepper motors. Spindle unit (120) may also be capable of generating rotation about third rotational axis δ (122), and/or rotation about second rotational axis θ (121), for example, using a semi-rotary drive and/or a semi-rotary actuator. Thus, spindle unit (120) may include a top portion (170) that can be attached to one or more motors or actuators to enable movement along the X-axis, the Y-axis, the Z-axis, the δ-axis, and/or the θ-axis.

As stated above, machining devices with fewer than six axes, or fewer than five axes, may be used. For example, a five-axis CNC machine that does not include one or more of the rotational axes may be used (e.g., a CNC machine that does not include third rotational axis δ (122) as shown in FIG. 1A). In other situations, a four-axis CNC machine that does not include a δ-rotational axis or a θ-rotational axis may be used. Such a CNC machine would include the three translational axes and the w-rotational axis as shown in FIG. 1A. Of course, machining devices which include fewer than four axes or more than six axes may also be used, as appropriate.

A machining device such as CNC machine (100) may be used, for example, to form an arthroplasty jig from an arthroplasty jig blank. In some instances, the arthroplasty jig may be a custom arthroplasty jig. Because of the complexity of some arthroplasty jigs' surfaces, especially custom arthroplasty jigs, it may be necessary to access multiple surfaces and/or sides of a jig blank from different angles to obtain the desired custom arthroplasty jig. By using the systems described herein, an arthroplasty jig blank can be positioned into a machining device in a way that allows one or more machining tools to access a body of the blank, while also securing the blank against movement even while under force or torque exerted on the blank by the machining process. Moreover, the systems described here may allow the arthroplasty jig blank to be positioned in a way that preserves one or more axes of the coordinate system of the machining device, such that the machine tools can operate and follow instructions in the machining device's reference frame. For example, a machine instruction to begin machining at a particular (X, Y, Z) coordinate in a specified direction may be applied directly to the jig blank, without a need to transpose coordinate systems, or to verify the position of the jig blank relative to the machine tool. Although the systems and methods described here are generally described for use in the manufacture of custom arthroplasty jigs, it is to be understood that the systems and methods can be applied to the manufacture of custom implants as well. Additionally, the systems and methods described here may be used to manufacture non-custom arthroplasty jigs and/or non-custom implants.

In certain variations, an arthroplasty jig manufacturing system may be used to provide enhanced arthroplasty jig manufacturing by a machining device. Generally, the arthroplasty jig manufacturing systems described here comprise a first positioning component. The first positioning component can be integral with, or configured to be coupled to, a machining device, such as a CNC machine similar to that illustrated in FIG. 1A, or a variant thereof. As used here, two components that are "integral with" each other includes two components that are part of a unitary body. Thus, the first positioning component can be formed directly onto a part of the machining device. Alternatively, the first positioning component can be a separate component that is affixed to, or coupled to, a part of the machining device.

The first positioning component can be integral with, or coupled to, any part of the machining device that allows movement of the first positioning component. For example, the first positioning component may be integral with, or coupled to, a shaft that can rotate and/or translate, a shaft that is coupled to a motor or actuator, a mounting plate or mounting surface that can rotate and/or translate, or a mounting plate or mounting surface that is coupled to a motor or actuator. Therefore, a motor or actuator that is part of the machining device can in turn drive motion of the first positioning component. Because movement of the first positioning component is driven by the machining device, the coordinate system of the machining device that includes its translational axes and its rotational axes can be preserved and transferred to the first positioning component. Thus, the coordinate system of the manufacturing device can also be transferred to a jig blank that is properly coupled to the first positioning component, as described below. As a result, instructions based on the machining device's coordinate system may be directly applied to the jig blank, without requiring coordinate system uncertainty or conversion. The result may be simplification and improved accuracy and precision during machining of the jig blank.

Figure 1B:
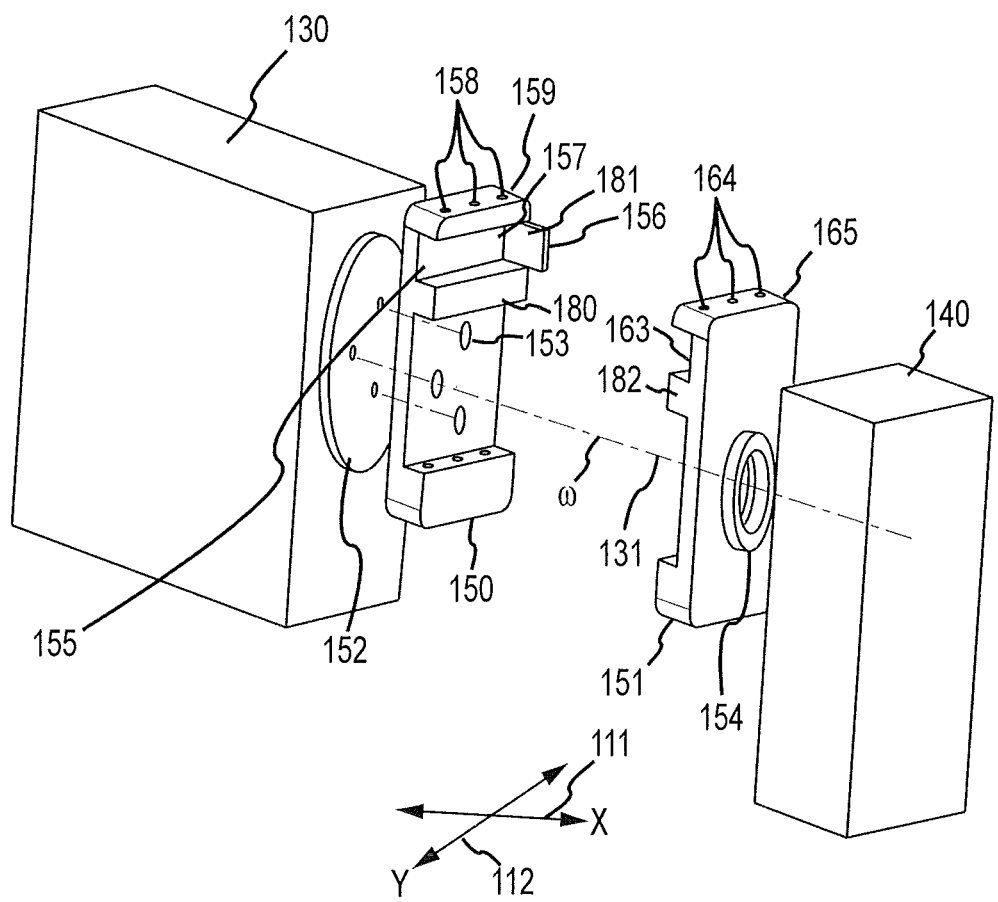
FIG. 1B is an enlarged view of the machining device and arthroplasty jig blank positioning components of FIG. 1A.

A variation of a first positioning component (150) is illustrated in FIG. 1A and again in a more enlarged view in FIG. 1B. First positioning component (150) is coupled to a rotatable shaft (not shown) that is driven by a rotary driver unit (130), so that first positioning component (150) can be rotated about first rotational axis ω (131). First positioning component (150) can be coupled to rotary driver unit (130) by any suitable method (e.g., by clamping, by one or more screws, mechanical locking, or adhesive). More than one securing method may be used, e.g., clamping combined with screws. In the variation shown in FIGS. 1A and 1B, first positioning component (150) is affixed to a mounting plate (152) with mounting screws (153). Mounting plate (152) is coupled to a rotatable shaft that is driven by rotary driver unit (130), so that a center of rotation of first positioning component (150) is aligned with first rotational axis ω (131).

As indicated above, the positioning components that are part of the systems described here are used to position a jig blank body of an arthroplasty jig blank in a machining device. In order to preserve and transfer one or more axes of the machining device coordinate system to the jig blank body, the positioning components can include one or more registration portions that are configured to receive, align and secure a jig blank coupled thereto. Thus, the positioning components have a positioning component body that is integral with, or configured to be coupled to, the machining device, and that comprises a first registration portion configured to couple with the arthroplasty jig blank. Coupling the first registration portion of the positioning component body with the arthroplasty jig blank positions the jig blank body along or about one or more axes of the machining device to allow for machining of at least a portion of the jig blank body.

For example, as shown in FIG. 1B, first positioning component (150) includes a positioning component body (180) that comprises a first registration portion (155) and a second registration portion (156). As shown, first registration portion (155) is in the form of a slot or groove having a surface (157) that can be aligned with a translational axis of the machining device (e.g., Y-axis (112)). Second registration portion (156) is configured as a stop having a surface (181) that also can be aligned with a translational axis of the machining device (e.g., X-axis (111)). It should be pointed out that positioning components with only a single registration portion can be used, where the single registration portion is configured to be aligned with a translational axis of the machining device. Also, positioning components with more than two registration portions may be used, for example a positioning component with three registration portions, each aligned with one of three orthogonal axes. Further, registration portions may contain additional features, such as demarcations indicating a scale, one or more positional stops, and/or one or more positional indicators or sensors.

Although the first registration portion is configured as a slot or groove and the second registration portion is configured as a stop in the illustrative variation shown in FIG. 1B, any suitable registration scheme may be used to receive, align and secure a jig blank that is coupled to it. As an example, a positioning component may include a protrusion that mates with an indentation on an arthroplasty jig blank. For example, a linear protrusion may mate with a slot or groove on the jig blank. As another example, a pin and socket configuration may be used, in which a positioning component includes a socket configured to receive one or more pins on a jig blank, or a jig blank includes a socket configured to receive one or more pins on a positioning component. Further, a single feature in a positioning component can include both a first and a second registration portion. As an example, a positioning component may include a groove parallel to the Y-axis of the machining device, wherein the groove includes a side wall parallel to the X-axis of the machining device.

A positioning component can secure an arthroplasty jig blank so that the position of the arthroplasty jig blank is ascertainable, accurate, and precise during the machining process, which can exert substantial force and/or torque on the jig blank. To that end, a positioning component may include one or more securing devices to secure the jig blank's position. Some variations of positioning components include one or more set screws that can be tightened against the jig blank to releasably secure the jig blank with or in the registration portion of the positioning component. For example, positioning component (150) in FIG. 1B includes set screws (158) that can be tightened from a top side (159) of the positioning component (150) to secure a jig blank (not shown) positioned in registration portion (155). While screws have been shown, a jig blank can be releasably secured in a registration portion of a positioning component using any suitable securing device. Non-limiting examples of such securing devices include clamping devices (e.g., a releasable clamp that is part of the positioning component, or a releasable clamp that is separate from the positioning component), or mechanical locks or brackets, or even adhesives. Combinations of securing devices may be used, e.g., a clamp combined with one or more screws, adhesives, and/or locks. In some cases, the configuration of the registration portion itself may be sufficient to secure the jig blank. For example, the jig blank may have a configuration that interlocks with the registration portion.

Certain variations of the systems described here can include two or more positioning components. For example, FIGS. 1A and 1B show a variation of a second positioning component. In the variation illustrated, the second positioning component (151) is coupled to a stabilizing unit (140) mounted on table (110) of CNC machine (100). In this case, second positioning component (151) is configured to rotate about first rotational axis ω (131). To this end, second positioning component (151) can be coupled to a rotational shaft that rotates about first rotational axis ω (131) in stabilizing unit (140). Second positioning component (151) can be coupled to stabilizing unit (140) using any suitable method (e.g., by screws, mechanical locking, or adhesive). For example, and as shown in FIG. 1B, second positioning component (151) includes a cylindrical member (154) that is configured to be concentric with first rotational axis ω (131) and to mechanically mate or lock with stabilizing unit (140) (e.g., on a mounting plate or mounting surface of the stabilizing unit that is coupled to a rotational shaft to allow rotation about first rotational axis ω (131)). Stabilizing unit (140) need not contain a motor or actuator to drive motion about or along an axis. Rather, stabilizing unit (140) can function to support an object affixed thereto while it is moved. For example, stabilizing unit (140) can contain a rotatable and/or translatable shaft that supports an object during rotation about first rotational axis ω (131) and/or translation along the X-axis and/or Y-axis. In some variations, stabilizing unit (140) may contain one or more motors or actuators to effect motion about or along one or more axes of CNC machine (100).

In systems that include a second positioning component, the second positioning component may comprise one or more registration portions that are configured to receive, align, and secure a jig blank while the jig blank is being positioned and/or machined. Thus, second positioning component (151) in FIG. 1B includes a second positioning component body (182) that comprises first registration portion (163). In the variation shown in FIG. 1B, first registration portion (163) is in the form of a groove or slot analogous to first registration portion (155) of the first positioning component (150). It should be noted that the registration portions of first and second positioning components may be the same as, or different from, each other. For example, one positioning component may have a registration portion configured as a slot, whereas a second positioning component in the same system may have a registration portion configured as a socket, or the like. Second positioning component (151) includes set screws (164) in a top portion (165) that are designed to releasably secure a jig blank (not shown) positioned in first registration portion (163). As described above with reference to the first positioning component, the one or more registration portions on the second positioning component may have any suitable configuration to receive, align, and secure a jig blank during manipulation and machining.

As indicated above, the arthroplasty systems described here are designed to be used with particular arthroplasty jig blanks. The arthroplasty jig blanks generally include an arthroplasty jig blank body and an arm fixture component that is integral with, or configured to be coupled to, the jig blank body. The arm fixture component is configured to couple to the first positioning component in such a way as to position the jig blank body for machining by the machining device. In some variations, arthroplasty jig blanks may be used that are suitable for use in forming multiple different types of arthroplasty jigs. For example, a single arthroplasty jig blank may be used to form either a knee arthroplasty jig or a hip arthroplasty jig.

Figure 2A:
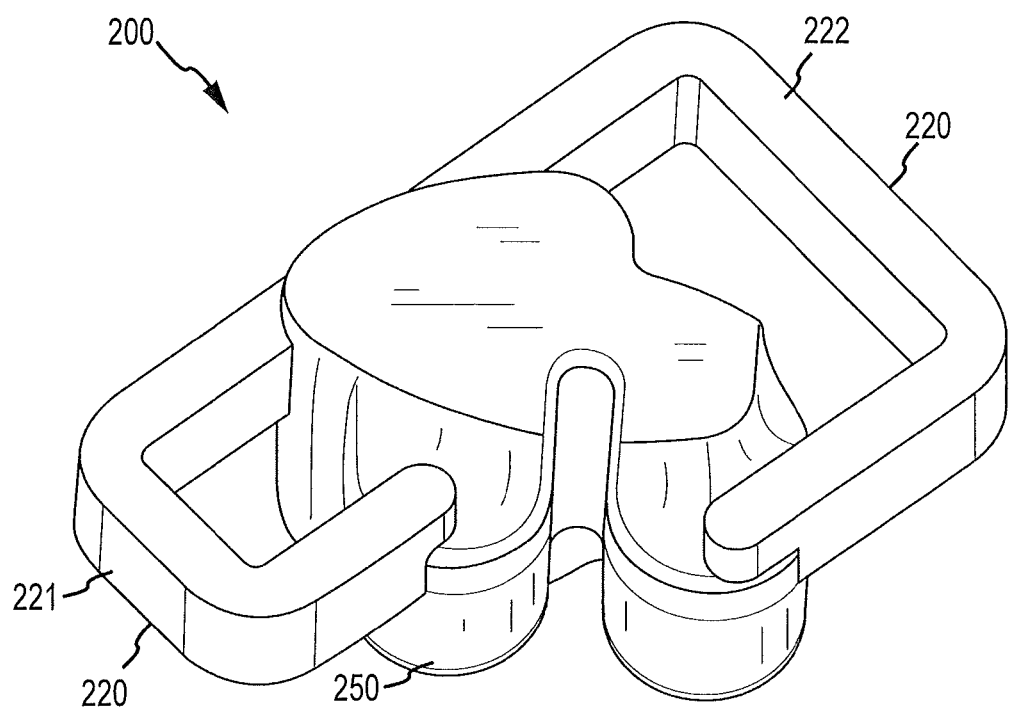
FIG. 2A is a top perspective view of a variation of a right tibial arthroplasty jig blank.
Figure 2B:
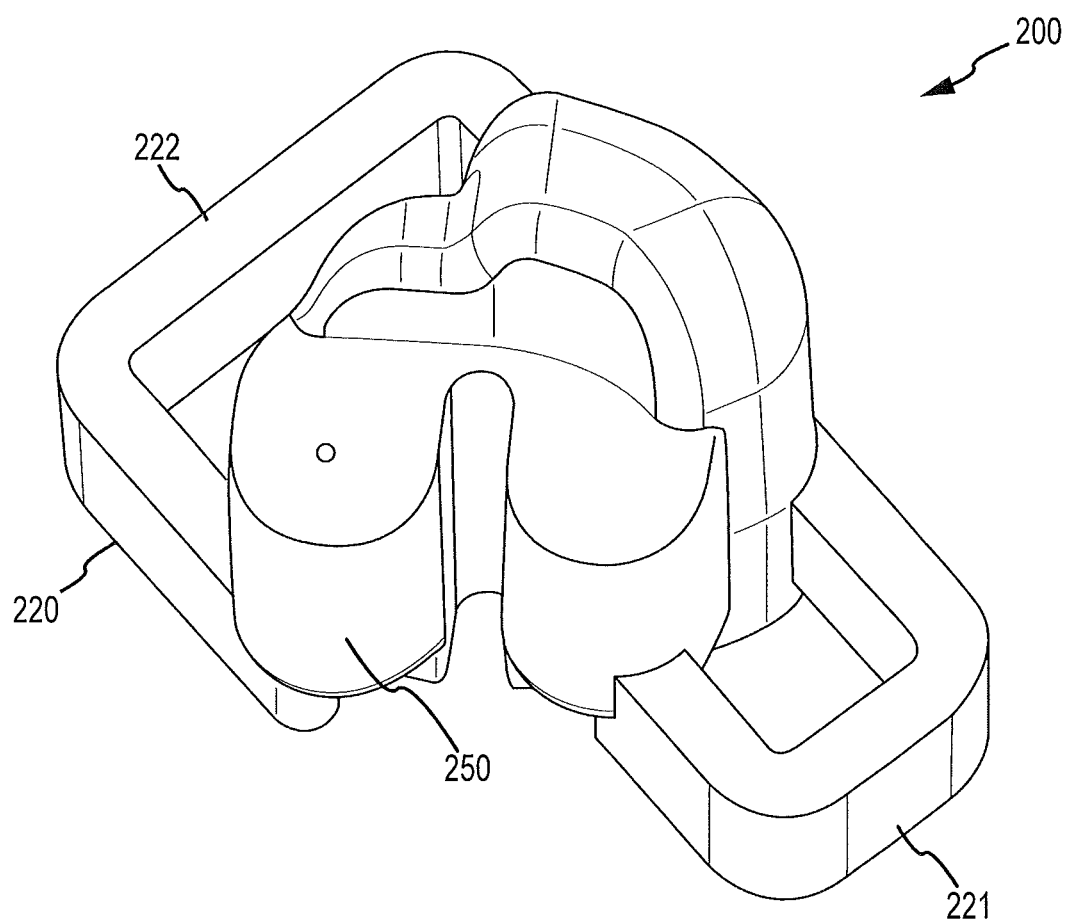
FIG. 2B is a bottom perspective view of the arthroplasty jig blank shown in FIG. 2A.

As a first illustrative variation, FIGS. 2A and 2B show an arthroplasty jig blank for use in making a right tibial arthroplasty jig. The jig blank (200) comprises a jig blank body (250) and an arm fixture component (220). Jig blank body (250) may be selected to have a shape, size, surface, and/or feature of the final desired arthroplasty jig, or that is close to that of the final desired arthroplasty jig. This may, for example, lead to reduced machining time, and/or to enhanced fit with a subject's anatomy. As an example, some variations of near-shape arthroplasty jig blanks are described in U.S. patent application Ser. No. 11/656,363, which has previously been incorporated herein by reference in its entirety. There, near-shape arthroplasty jig blanks are described that have one feature specific to a target anatomy site to be matched by the arthroplasty jig. In the variation shown in FIGS. 2A and 2B, arm fixture component (220) comprises a first U-shaped member (221) and a second U-shaped member (222), with the second U-shaped member extending 180° opposed from the first U-shaped member.

Figure 3A:
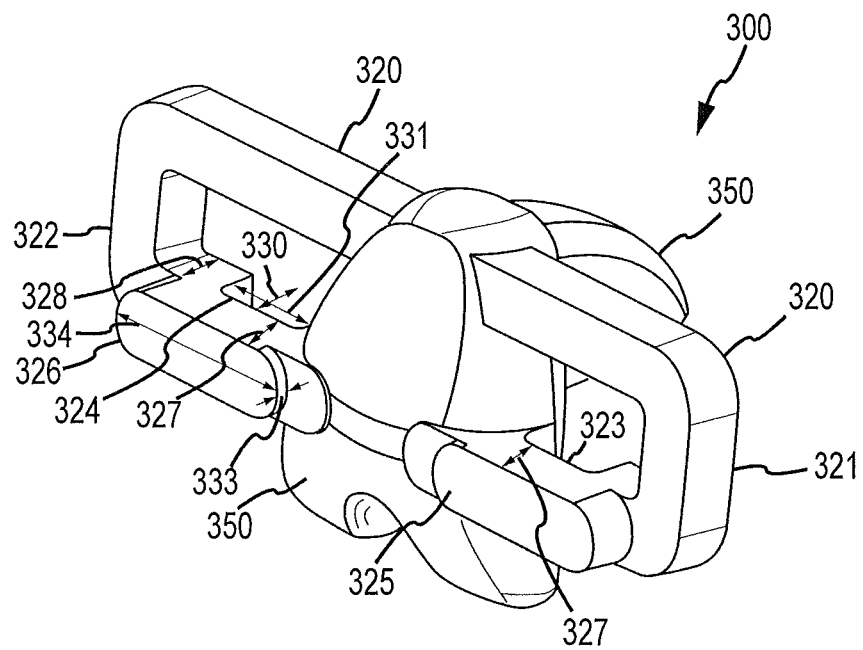
FIG. 3A is a front perspective view of a variation of a left femoral arthroplasty jig blank.
Figure 3B:
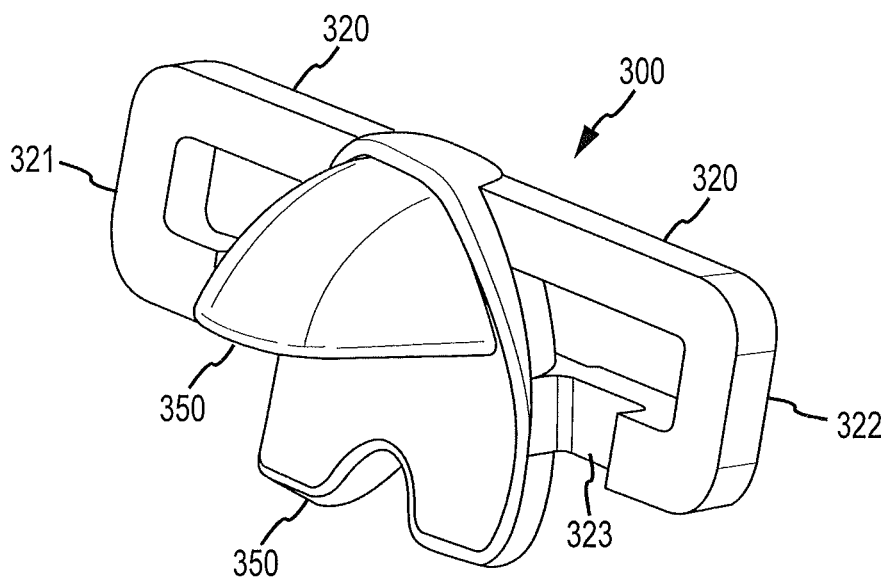
FIG. 3B is a rear perspective view of the arthroplasty jig blank shown in FIG. 3A.

As another illustrative variation, FIGS. 3A and 3B show an arthroplasty jig blank (300) for use in making a left femoral arthroplasty jig. As shown there, jig blank (300) comprises a jig blank body (350) and an arm fixture component (320). Again, the arm fixture component comprises a first U-shaped member (321) and a second U-shaped member (322) extending 180° opposed from the first U-shaped member. The arthroplasty jig blank shown in FIGS. 3A and 3B has a first recessed region (323) and a first protrusion (325) in the first U-shaped member (321) of arm fixture component (320), and a second recessed region (324) and a second protrusion (326) in second U-shaped member (322). The recessed regions (323) and (324) may, for example, allow improved machine tool access to certain portions of jig blank body (350). The recessed regions (323) and (324) may have any appropriate depth and width, such as depth (330) and width (331) of recessed region (324). For example, one or both of the recessed regions may have a depth that is similar to a thickness (e.g., 328) of the arm fixture component (e.g., about 10 mm). In other variations, one or both of the recessed regions may have a depth that is less than a thickness of the arm fixture component. The width of one or both of the recessed regions may be selected to allow desired access to jig blank body (350). For example, one or both of the recessed regions may have a width of about 1 cm to about 2 cm.

Protrusions (325) and (326) may provide improved support in arm fixture component (320) by adding to the arm fixture component thickness near or at the location of one or both recessed regions. For example, in some variations, protrusion (326) may have a depth (333) such that the arm fixture component thickness (327) near or at recessed region (324) may be approximately the same as the arm fixture component thickness (328) beyond recessed region (324). Protrusions may have depths and widths sufficient to reinforce the arm fixture component. For example, protrusion depths may be about 0.5 mm to about 3 mm, and/or protrusion widths may be about 1 cm to about 4 cm.

Some variations of arm fixture components may have recessed regions without corresponding protrusions. Other variations of arm fixture components may have protrusions to strengthen certain portions of the arm fixture component even without the presence of recessed regions. Although recessed regions and protrusions have been shown being used in an arm fixture component having U-shaped members in this example, recessed regions and strengthening protrusions may be used with any suitable configuration of arm fixture component. Further, although the example shown in FIGS. 3A and 3B has two recessed regions (323) and (324) and two protrusions (325) and (326) positioned on opposite sides of jig blank body (350), variations may be used that have only a single recessed region and/or a single protrusion or that have more than two recessed regions and/or protrusions.

As with the tibial jig blank, the femoral jig blank body (350) may be selected to have a shape, size, surface, and/or feature of the final desired arthroplasty jig or that is close to that of the final desired femoral arthroplasty jig to reduce machining time and/or provide an enhanced fit with a subject's anatomy.

Figure 4A:
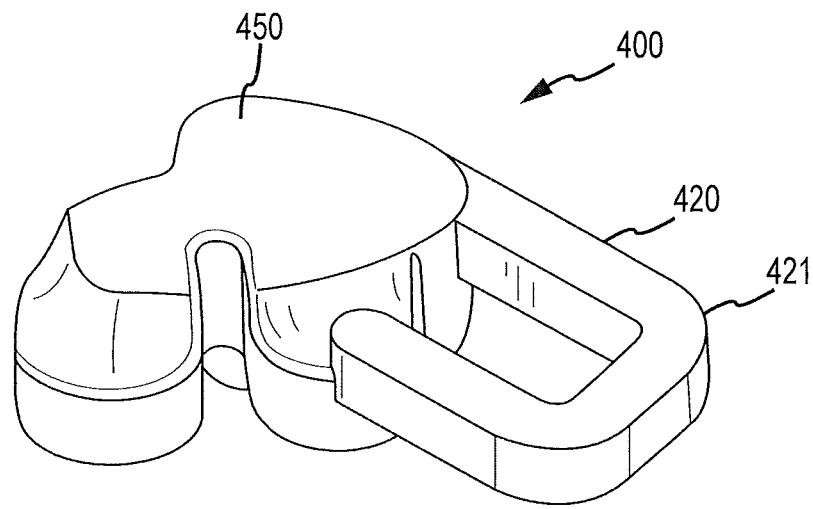
FIGS. 4A and 4B illustrate another variation of a left tibial arthroplasty jig blank.
Figure 4B:
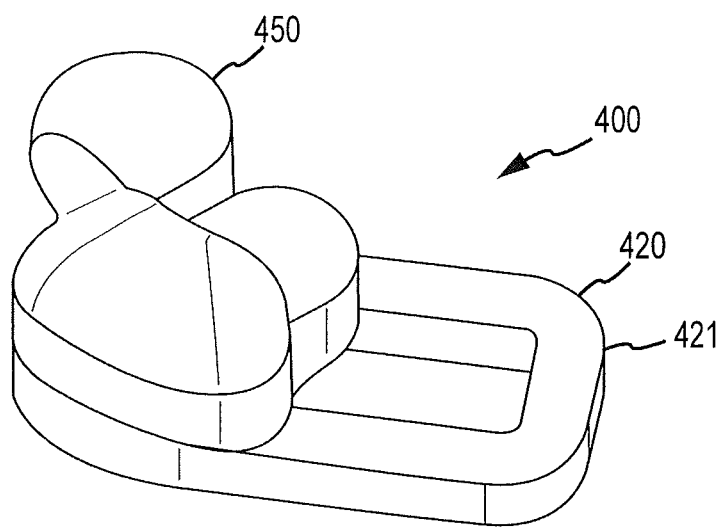
Figure 5A:
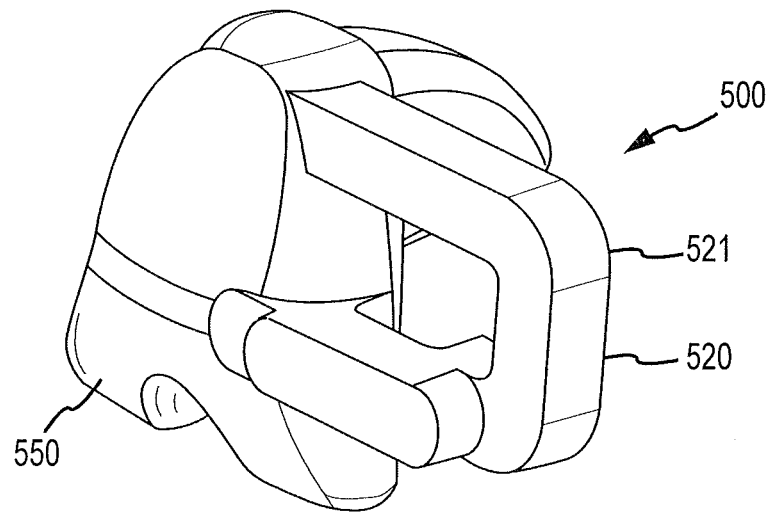
FIGS. 5A and 5B illustrate another variation of a left femoral arthroplasty jig blank.
Figure 5B:
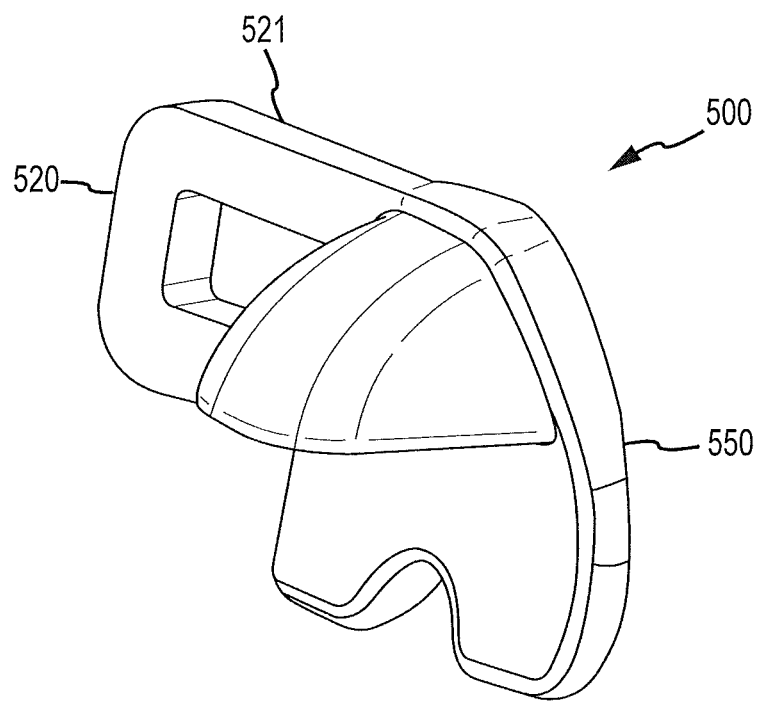

Other variations of arthroplasty jig blanks are illustrated in FIGS. 4A-4B and 5A-5B. FIGS. 4A and 4B show a tibial jig blank (400) having a jig blank body (450) and an arm fixture component (420). Arm fixture component (420) has only a single U-shaped member (421) coupled to, or integral with, jig blank body (450). FIGS. 5A and 5B show a femoral jig blank (500) comprising a jig blank body (550) and an arm fixture component (520). Arm fixture component (520) has only a single U-shaped member (521) coupled to, or integral with, jig blank body (550). Other variations of arthroplasty jigs having different configurations of arm fixture components may also be used, as appropriate.

Generally, in the systems described here, the arm fixture components are configured to be coupled to the first positioning components in such a way as to preserve at least one axis of the coordinate system of the machining device. This allows the same axis in the same coordinate system to be used while machining the jig blank. In some variations of the systems, at least two axes of the coordinate system of the machining device (e.g., two translational axes, or one rotational axis and one translational axis) are preserved when the arm fixture component of the jig blank is coupled to the first positioning component. In still other variations, at least three axes of the coordinate system of the machining device (e.g., two translational axes and a rotational axis) are preserved when coupling the jig blank arm fixture component to the first positioning component. In some cases, at least four axes of the machine device coordinate system (e.g., three translational axes and a rotational axis) are preserved upon coupling the arm fixture component to the first positioning component. By utilizing the same reference frame for both the machining device and the arthroplasty jig blank, machining instructions in the machining device's coordinate system or machining instructions in an arthroplasty jig blank coordinate system can be used. This may simplify the process for creating machining instructions. It also may reduce the need to verify the position of the jig blank during the machining process, and reduce the likelihood of translation errors occurring when converting from one coordinate system to another.

To preserve one or more axes of the machining device's coordinate system, and transfer this frame of reference to the jig blank for machining, the arm fixture component and the positioning component may be coupled to each other in a particular way. As an example, a registration portion of the positioning component can align and position the arm fixture component of the jig blank so that the jig blank body can be moved and machined along or about the one or more axes of the machine coordinate system, to allow machining of at least a portion of the jig blank body.

Figure 6A:
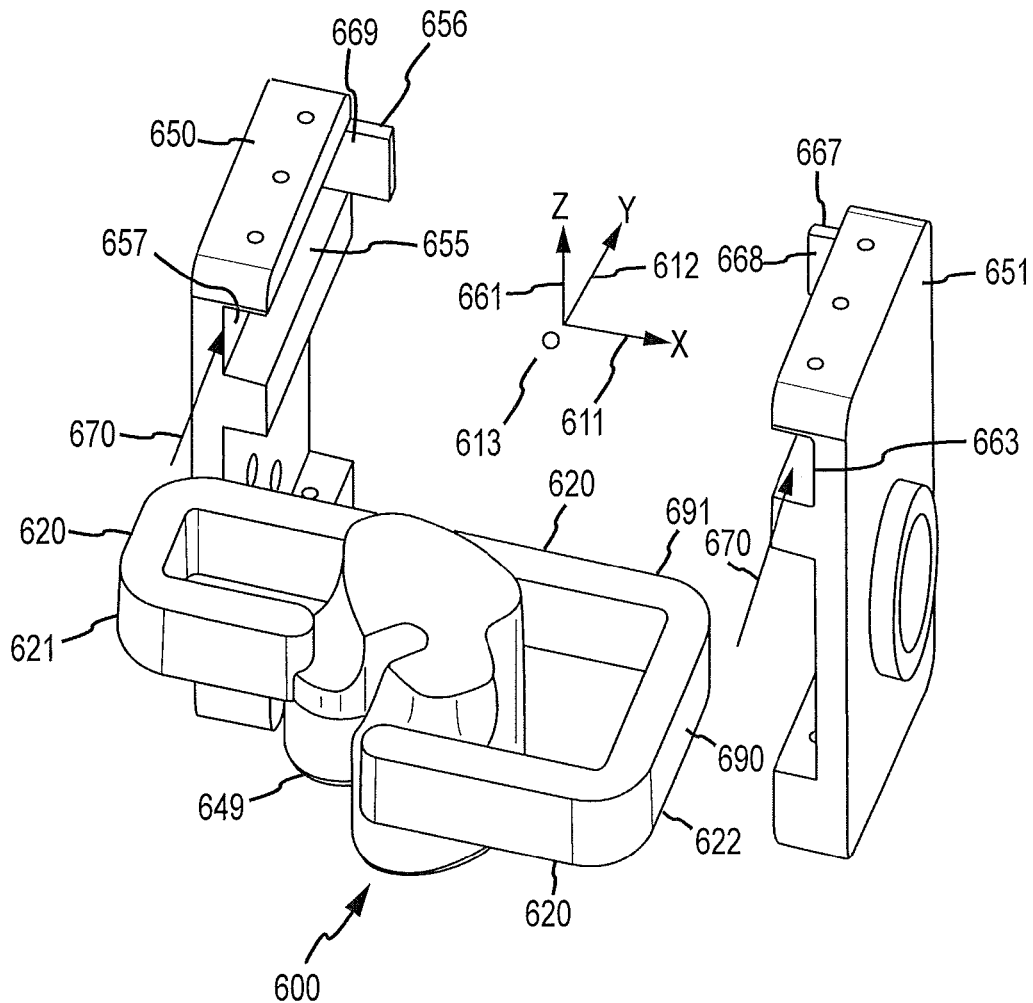
FIG. 6A illustrates a pair of positioning components, and an arthroplasty jig blank that can be coupled to the pair of positioning components.
Figure 6B:
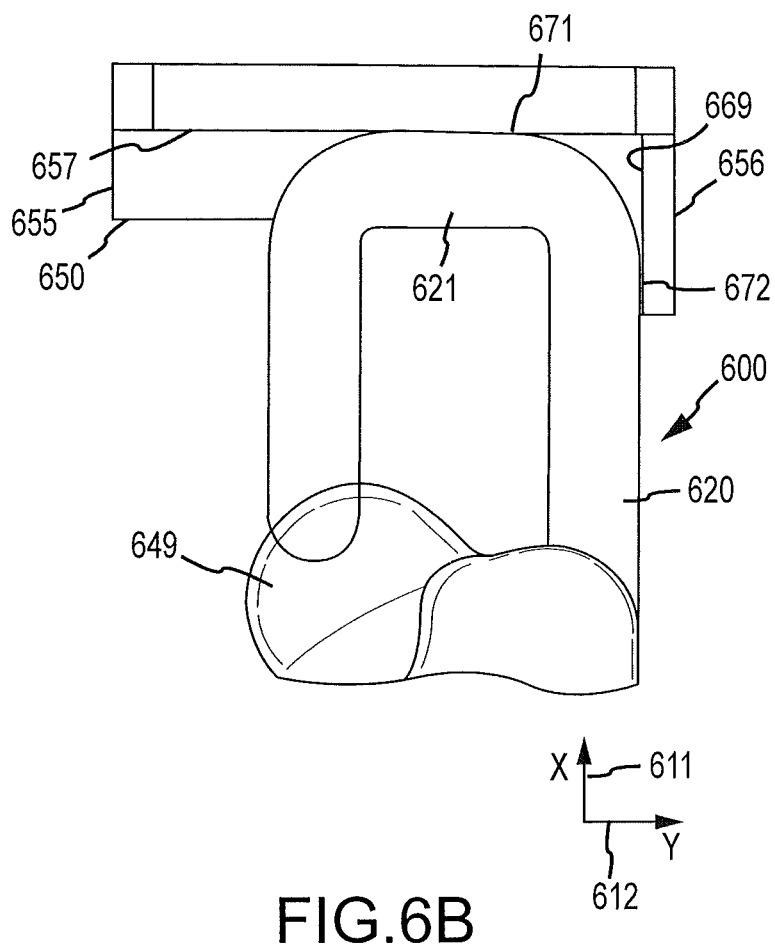
FIG. 6B shows an alternate view of a portion of an arthroplasty jig blank being coupled to a positioning component.
Figure 6C:
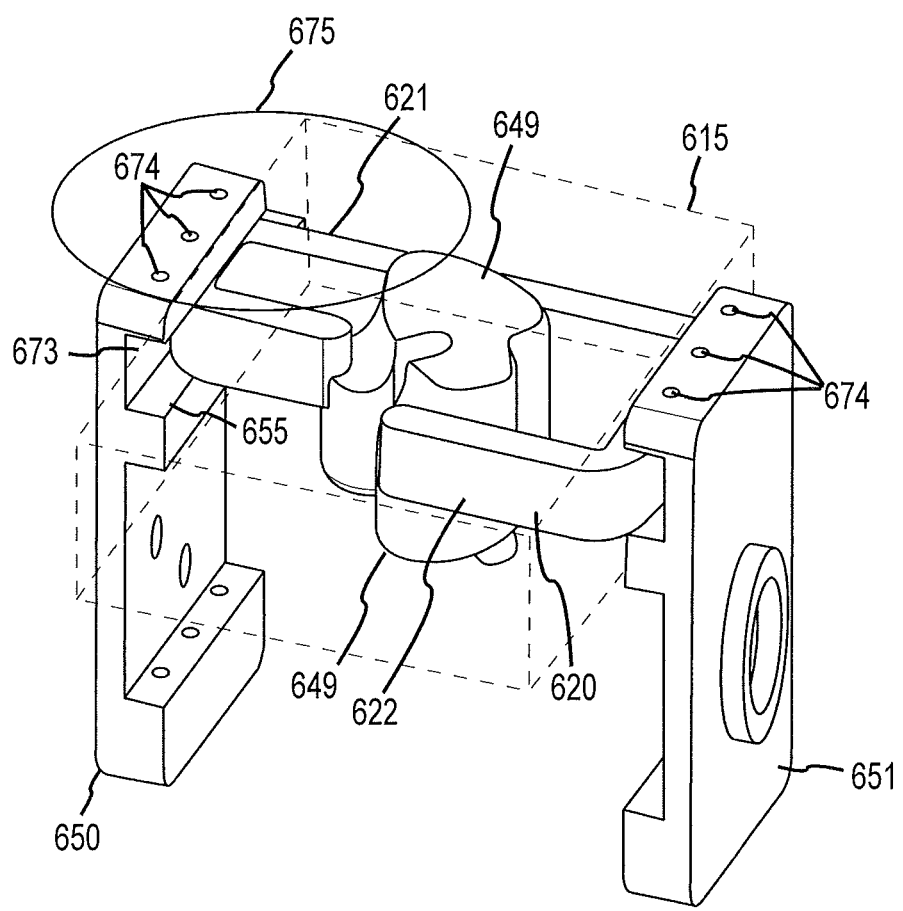
FIG. 6C shows an arthroplasty jig blank that has been coupled to a pair of positioning components.

FIGS. 6A, 6B, and 6C illustrate an example of a method of mounting an arthroplasty jig blank (600) into a first positioning component (650) and a second positioning component (651). Arthroplasty jig blank (600) comprises an arm fixture component (620) and a jig blank body (649). In this variation, arm fixture component (620) has a first U-shaped member (621) and a second U-shaped member (622). First positioning component (650) has a first registration portion (655) in the form of a slot or groove having a surface (657) that can be aligned with the Y-axis (612) of a machining device (not shown). In this variation, first positioning component (650) also has a second registration portion (656) in the form of a stop having a surface (669) that can be aligned with the X-axis (611) of the machining device. Second positioning component (651) has a first registration portion (663) in the form of a slot having a surface that can also be aligned with the Y-axis, and a second registration portion (667) in the form of a stop having a surface (668) that can be aligned with the X-axis. In this variation, as arrows (670) indicate, arm fixture component (620) of jig blank (600) is configured to slidably engage with first registration portion (655) of first positioning component (650) to abut second registration portion (656), and to slidably engage with first registration portion (663) of the second positioning component (651) and abut second registration portion (667). By doing so, jig blank body (649) can be aligned with two translational axes (e.g., X- and Y-axes) of the machining device.

Further, an origin (613) of one or more of the translational axes of the machining device (e.g. the X-axis (611), Y-axis (612), and Z-axis (661)) can be set when the jig blank is mounted into a positioning component and aligned with the use of one or more registration portions of the positioning component. For the variation shown in FIGS. 6A-6C, the origin can be set when the arm fixture component is inserted into registration portions (655) and (663) to align with the Y-axis, and abuts registration portions (656) and (667) to align with the X-axis. Thus, the origin used in machine files that are input into the machining device to deliver cutting, milling, and drilling instructions can be made to correspond to the origin of a jig blank body so positioned in the machining device.

To preserve and transfer the machining device's coordinate system from the positioning component to the jig blank, the arm fixture component to be coupled to the positioning component has one or more surfaces configured to align with the one or more registration portions of the positioning component. Thus, as illustrated in FIGS. 6A and 6B, arm fixture component (620) of jig blank (600) has first U-shaped member (621) having a first planar surface (671) configured to align with a first planar surface (657) of first registration portion (655) of first positioning component (650). First planar surface (657) of the first registration portion (655) is aligned with the Y-axis (612) of the machining device. First U-shaped member (621) also has a second planar surface (672) that is configured to align with a second planar surface (669) of the first positioning component's second registration portion (656). Second planar surface (669) is in turn aligned with the X-axis (611) of the machining device. Similarly, second U-shaped member (622) of arm fixture component (620) has a planar surface (690) configured to be aligned with a planar surface of the second positioning component's first registration portion (663). Planar surface (690) is in turn aligned with the Y-axis (612) of the machining device. Second U-shaped member (622) has another planar surface (691) configured to be aligned with surface (668) of the second positioning component's second registration portion (667), where surface (668) is aligned with the X-axis (611) of the machining device.

Therefore, and as illustrated in FIG. 6C, when arm fixture component (620) is slidably engaged into first registration portions (655) and (663) of the first and second positioning components (650) and (651), respectively, to abut surfaces (669) and (668) of second registration portions (656) and (667), respectively, and secured (e.g., with set screws (674) shown in the encircled region (675)), at least a portion of jig blank body (649) can be machined. As indicated approximately by the volume (615), a significant volume of jig blank body (649) can be accessed by one or more machining tools of the machining device.

As described here, the volume of the jig blank body that can be accessed by one or more machining tools in this way may also be referred to as a "workable volume" of the jig blank body. In some variations, systems described here may allow about at least about 10 cubic inches, at least about 15 cubic inches, at least about 20 cubic inches, at least about 25 cubic inches, at least about 30 cubic inches, at least about 35 cubic inches, at least about 40 cubic inches, at least about 45 cubic inches, at least about 50 cubic inches, at least about 55 cubic inches, or at least about 60 cubic inches of workable volume on the jig blank. Positioning components (650) and (651) can be rotated 360° about rotational axis ω of the machining device to allow access to the workable volume from multiple angles.

Figure 7:
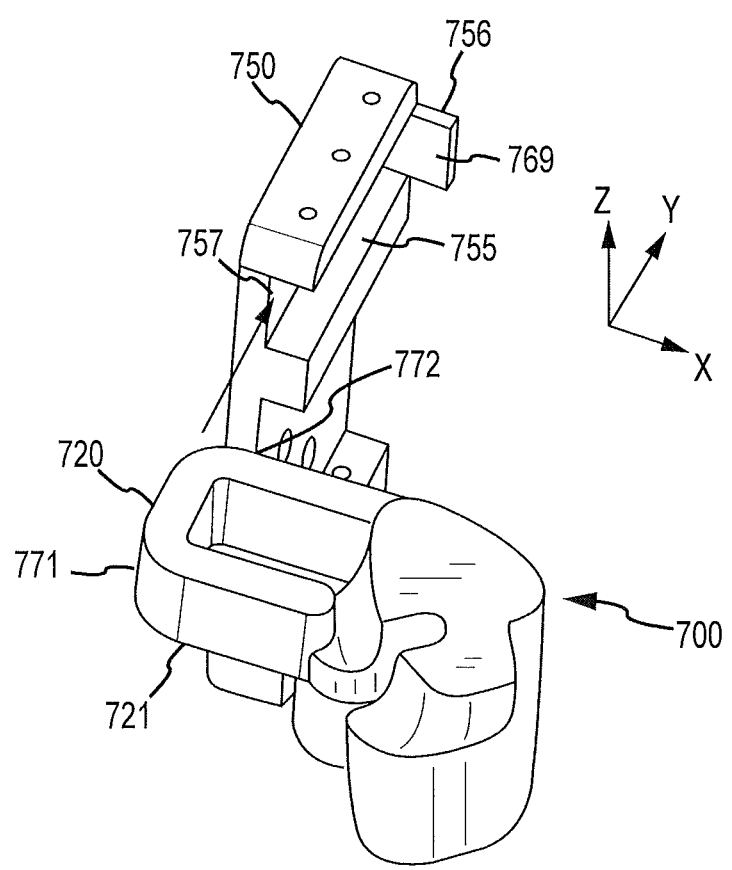
FIG. 7 shows a single positioning component and a variation of an arthroplasty jig blank that can be coupled to the single positioning component.

In other variations of the systems, only one positioning component may be used to receive, align, and secure a jig blank body while machining. An example of such a variation is shown in FIG. 7. There, a first positioning component (750)

has a first registration portion (755) in the form of a slot having a planar surface (757) that can be aligned with the Y-axis of a machining device (not shown). First positioning component (750) also has a second registration portion (756) having a planar surface (769) that can be aligned with the X-axis of the machining device. An arthroplasty jig blank (700) has an arm fixture component (720) having a single U-shaped member (721). U-shaped member (721) has a first planar surface (771) that can be aligned with surface (757) of first registration portion (755) to align with the Y-axis of the machining device. U-shaped member (721) also has a second orthogonal planar surface (772) that can be aligned with surface (769) of second registration portion (756) to align with the Y-axis of the machining device.

By using only one positioning component, it may be possible to increase accessible volume of the jig blank body for machining. In addition, systems using only one positioning component may be configured to couple with arm fixture components extending from only one side of a jig blank body (e.g., a single U-shaped member instead of two, opposed U-shaped members). This may, for example, result in relatively easy removal of the arm fixture component from the jig blank to form a final arthroplasty jig. As a result, machining time to remove the arm fixture component from only one side of the jig blank may be reduced.

In the systems described here, the arm fixture components of the arthroplasty jig blanks may have any suitable configuration to position the jig blank body into a machining device (e.g., to preserve one or more axes of the machining device's coordinate system), and/or to stabilize the jig blank body from the force and torque it can experience during machining. For example, a spindle unit rotating at about 12,000 rpm can generate between about 5 to about 15 pounds of vertical force. Thus, it may be desirable for an arm fixture component to be able to provide support along multiple axes to cause minimal deformations and movements (e.g., of less than about 0.1 mm, or less than about 0.08 mm, or less than about 0.06 mm, or less than about 0.04 mm, or even less than about 0.02 mm). Providing such support may aid in the accurate machining of any feature, especially detailed features that have small dimensions (e.g., less than about 2 mm, or less than about 1 mm, or less than about 0.5 mm, or even smaller). In addition, arm fixture components typically are removed from the jig blank body when machining is complete to form the final customized arthroplasty jig. Therefore, to reduce the time for removal of the arm fixture component (e.g., by machining), it may be desired to reduce the area of contact between the jig blank body and the arm fixture component.

Different variations of arm fixture component designs other than those shown above may be used in combination with a positioning component such as that shown in FIGS. 1A and 1B to align, position and support a jig blank body along one or more axes of a machining device. For example, arm fixture components can include other features, such as drilling holes or slots that can increase machine tool access to the jig blank body. Some illustrative, non-limiting examples of arm fixture components are provided in FIGS. 8A-8E.

Figure 8A:
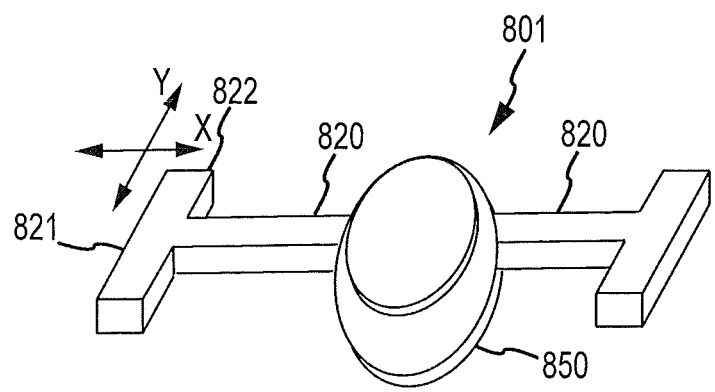
FIGS. 8A-8E depict various configurations of arthroplasty jig blanks having different arm fixture component designs.
Figure 8B:
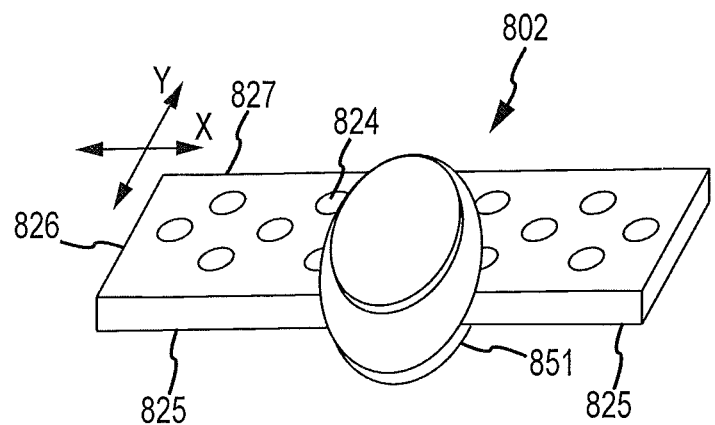
Figure 8C:
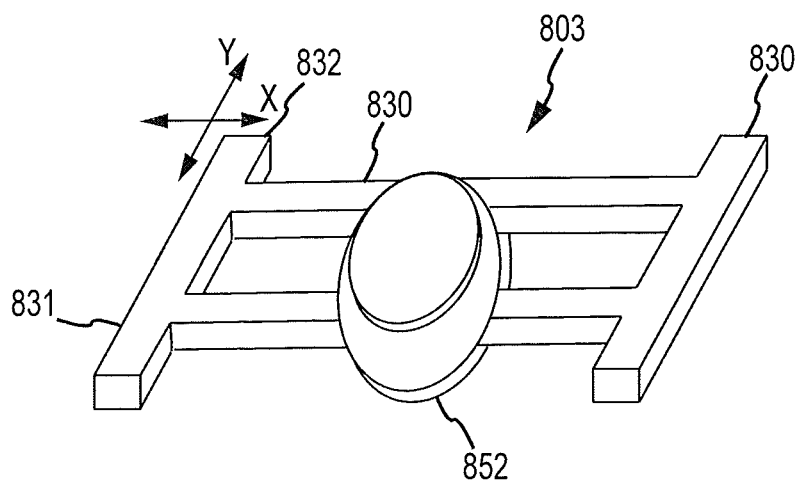
Figure 8D:
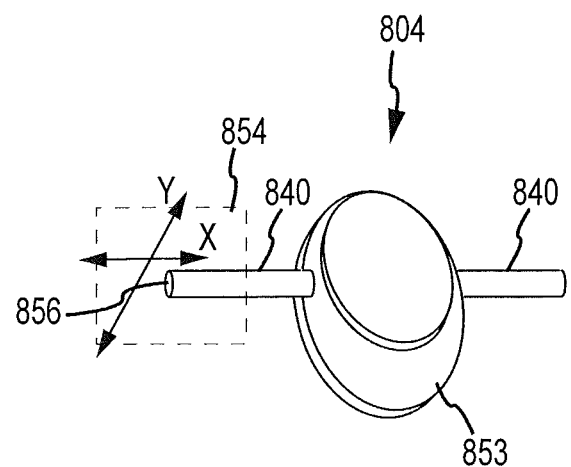
Figure 8E:
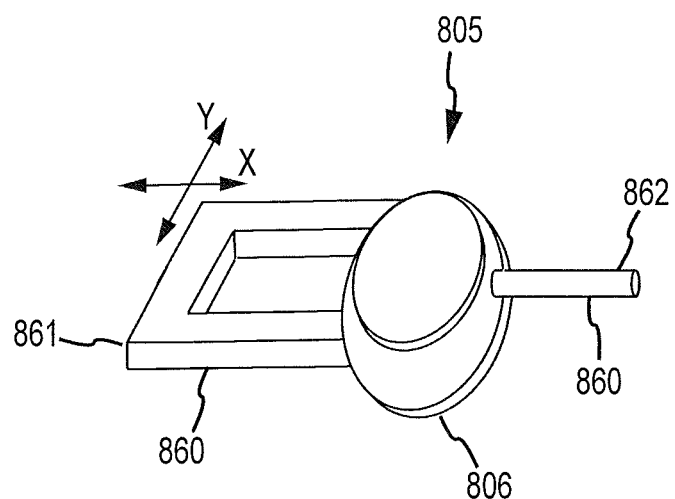

FIG. 8A shows a jig blank (801) having a T-shaped arm fixture component (820) integral with, or coupled to, a jig blank body (850). Arm fixture component (820) has a first planar surface (821) that can be parallel to a Y-axis of a machining device, and a second orthogonal planar surface (822) that can be parallel to an X-axis of a machining device. FIG. 8B shows a jig blank (802) having a rectangular-shaped arm fixture component (825) that is integral with, or coupled to, a jig blank body (851). Arm fixture component (825) has two orthogonal planar surfaces (826) and (827) that can be parallel to Y- and X-axes of a machining device, respectively. The rectangular-shaped arm fixture component can include one or more perforations (824) to reduce bulk, and to decrease contact area between the jig blank body and the arm fixture component, thereby facilitating removal of the arm fixture component. FIG. 8C shows a jig blank (803) having a π-shaped arm fixture component (830) that is integral with, or coupled to, a jig blank body (852). Again, π-shaped arm fixture component (830) has a first planar surface (831) and a second orthogonal planar surface (832) that can be aligned with Y- and X-axes, respectively, of the machining device. FIG. 8D shows a jig blank (804) having a rod-like arm fixture component (840) that is integral with, or coupled to, jig blank body (853). Rod-like arm fixture component (840) has a planar face (856) that is orthogonal to a plane (854) that is tangent to a curved side of the arm fixture component. Thus, planar face (856) can be aligned with a Y-axis of the machining device, and tangent plane (854) can be aligned with an X-axis of the machining device.

Of course, and as shown in FIGS. 2A-2B and 3A-3B, the arm fixture component need not be symmetrical from side to side, top to bottom, and/or front to back. Therefore, any combination of arm fixture components may be used in a single jig blank. For example, in FIG. 8E, a jig blank (805) is illustrated that has an arm fixture component (860) having a U-shaped member (861) extending from one side of the jig blank body (806) and a rod-like member (862) extending from the opposite side of the jig blank body (806). Any other suitable configurations may also be used.

Figure 9A:
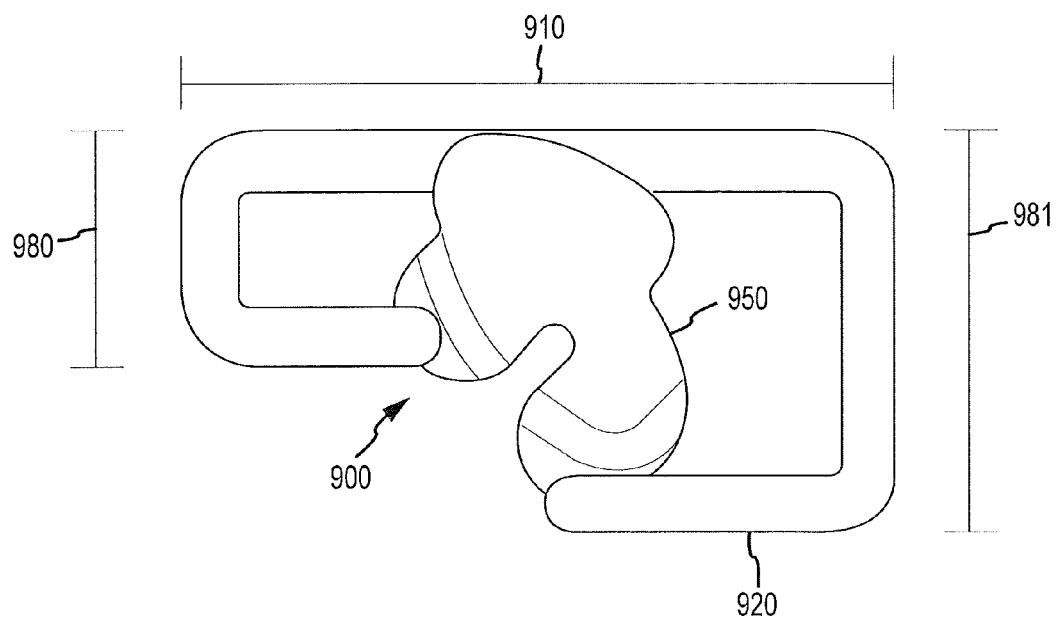
FIG. 9A is a top view of a variation of an arthroplasty jig blank.
Figure 9B:
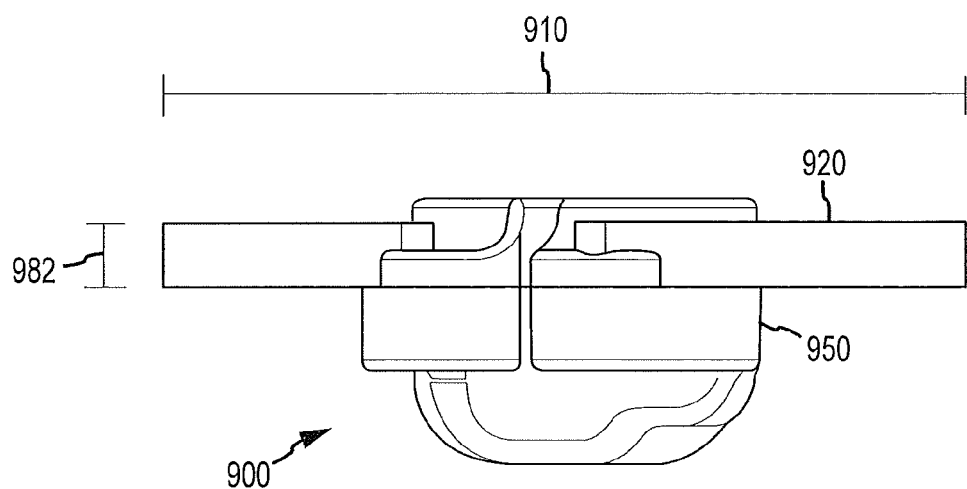
FIG. 9B is a rear side view of the arthroplasty jig blank of FIG. 9A.

The dimensions of the arm fixture component on an arthroplasty jig blank may be selected based on the type and/or size of the arthroplasty jig involved, and/or the material used, and/or the dimensions of the corresponding positioning component. FIGS. 9A and 9B show a tibial jig blank having a jig blank body (950) and an arm fixture component (920). A length-wise cross-sectional dimension (910) of arm fixture component (920), which allows jig blank (900) to be connected between two positioning components (not shown), may in part determine the workable volume of jig blank body (950). In some variations, jig blanks can be provided that have a length-wise cross-sectional dimension of about 4 inches to about 8 inches (e.g., about 4 inches, about 5 inches, about 6 inches, about 7 inches, or about 8 inches). In some cases, the length-wise cross-sectional dimension can be even smaller (e.g., about 3 inches), or larger (e.g., about 9 inches or 10 inches). A longer length-wise dimension is suitable for use with relatively spaced-apart positioning components. While the longer lever arm may decrease the jig blank's ability to withstand force or torque during machining, it may also increase the volume accessible by one or more machining tools. A widthwise cross-sectional dimension of the arm fixture component of the jig blank (e.g., dimensions (980) and (981) in FIG. 9A) can in part determine the jig blank's ability to resist non-normal force or torque while machining. In certain variations, jig blanks may be used that have an arm fixture component having a widthwise cross-sectional dimension (980) or (981) of about 1 inch to about 6 inches (e.g., about 1 inch, about 2 inches, about 3 inches, about 4 inches, about 5 inches, or about 6 inches).

The arm fixture component may have any suitable thickness (dimension (982) in FIG. 9B), again based on the type and/or size of arthroplasty jig being manufactured, and/or the material used, and/or the corresponding positioning component used with the arthroplasty jig blank. A thicker arm fixture component may be better able to stabilize the jig blank against movement, bending, and/or deformation caused by force and/or torque from the machining process. However, a thicker arm fixture component may also take longer to remove from the jig blank body. In some variations, jig blanks having arm fixture components with thicknesses of about 10 mm to about 20 mm (e.g., about 12 mm, about 14 mm, about 16 mm, or about 18 mm) may be used. In some cases, thicknesses of less than 10 mm (e.g., about 8 mm), or more than 20 mm (e.g., about 22 mm), may be used. Of course, the dimensions used for the arm fixture component may depend on the material used. For example, a stiffer material may require less thickness to provide the necessary level of stability and deformation resistance than a compliant material. As an example, an arthroplasty jig blank made from Delrin™ polymer having an arm fixture component with a configuration similar to that shown in FIGS. 2A and 2B or 3A and 3B, a thickness of about 10 mm to about 20 mm, and length-wise cross-sectional dimension of about 4 inches to about 8 inches, is expected to exhibit acceptable stability and deformation resistance under typical machining forces (e.g., about 5 to about 15 pounds of vertical force).

Any suitable material may used to form the arthroplasty jig blanks. For example, biocompatible polymers may be used as they may be relatively easy to machine. Examples of biocompatible polymers that can be used include as acetal resins, e.g., Delrin™, Nylon™ polycarbonates, polyetheretherketones (PEEK), polyethylenes, polypropylenes, Teflon™, polystyrenes, polyacrylates, polyamides, polyesters, polyurethanes, vinyl polymers, and combinations or blends thereof may be used. In other situations, an easily machinable biocompatible metal may be used to form the jig blanks, such as aluminum. More than one material may be used in an arthroplasty jig, e.g., the arm fixture component may be formed from a different polymer from the jig body.

Methods for manufacturing an arthroplasty jig by machining are also provided. The methods can incorporate the use of automated machining devices, such as CNC machines, to rapidly and accurately machine a custom arthroplasty jig. The methods can be used to make any type of arthroplasty jig, such as a knee arthroplasty jig (tibia or femur), a hip arthroplasty jig, an elbow arthroplasty jig, or a spinal arthroplasty jig.

The methods include coupling an arm fixture component of an arthroplasty jig blank to a first positioning component that is coupled to, or integral with, a machining device. The first positioning component is adjusted to position a jig blank body of the arthroplasty jig along or about one or more axes of the machining devices. In many cases, the machining device is a CNC machine, and the positioning component is adjusted automatically by instructions input into the CNC machine. The instructions may be used to position the jig blank body using one or more axes of the coordinate system of the machining device. For example, the first positioning component can be rotated 360° about a first rotational axis of the machining device to facilitate machine tool access to the body of the jig blank.

The methods include machining at least a portion of the jig blank body with one or more machining tools of the machining device to form the arthroplasty jig. After the surfaces of the arthroplasty jig blank body have been machined as desired, the arm fixture component can be removed from the jig blank body (e.g., by cutting the arm fixture component off with a milling tool or other cutting tool). Some methods can include coupling the arm fixture component of the arthroplasty jig blank to a second positioning component that is coupled to, or integral with, the machining device. Any suitable commercially available software may be used to provide instructions to the machining device, e.g., Visualmill, available from Mecsoft Corp. Irvine, Calif. (www.mecsoft.com), SolidCAM, available from www.solidcam.de, Camworks™, available from Geometric Technologies, Scottsdale, Ariz., www.teksoft.com, AutoCAM, available from Compass Solutions, Ltd., www.compasssolutions.co.uk/AutoCAM/html, and others.

A variation of a method of machining an arthroplasty jig is illustrated in FIG. 10. FIG. 10 shows a first positioning component (1050) coupled to a rotary driver unit (1030) of a CNC machine (1000) mounted on an X-Y table (1040), such that the first positioning component can rotate around the machining device's first rotational axis w. An arthroplasty jig blank (1010) is coupled to first positioning component (1050) via an arm fixture component (1020).

Arm fixture component (1020) is mounted into first positioning component (1050) in such a manner as to align the jig blank body with first and/or or second translational axes of CNC machine (1000). As a result, those axes of the machining device can be used to machine the jig blank body without need for coordinate transformation. Thus, the method can simplify the process of creating and delivering instructions for the machining of the jig blank. For example, the arm fixture component can be aligned with a first translational axis of CNC machine (1000) by aligning a face (not shown) of the arm fixture component (1020) with a face (1057) of a first registration portion (1055) of a first positioning component (1050) that is aligned with the Y-axis. Arm fixture component (1020) can be aligned with a second translational axis of CNC machine (1000) by providing a face of a second registration portion (not shown) that is orthogonal to face (1057) of the first registration portion and aligned with the X-axis of CNC machine (1000). Once the arm fixture component is coupled to the first positioning component so that the jig blank body is aligned with one or more axes of CNC machine (1000), it can be secured in place in the positioning component (e.g., by using set screws (1004) or a clamp). Thus, jig blank (1010) and, therefore, jig blank body (1015), are aligned with the first rotational axis w, the first translational axis X, and the second translational axis Y of CNC machine (1000).

Optionally, the methods can include coupling the arm fixture component (1020) to a second positioning component (1051) that is in turn coupled to a stabilizing unit (1080) of CNC machine (1000). Coupling the arm fixture component between a first and a second positioning component may provide increased stability during movement of the jig blank, and especially during machining of the jig blank as the jig blank is rotated about rotational axis w.

After the jig blank is securely mounted into one or more positioning components coupled to CNC machine (1000) so that jig blank is aligned with one or more axes of CNC machine (1000), the methods include applying one or more machining tools to the jig blank body to form a custom arthroplasty jig. Referring again to FIG. 10, a spindle unit (1060) comprising an interchangeable cutting, milling, or drilling tool (1059) can be translated along the Z-axis, (e.g., raised and lowered), to access and machine the jig blank body (1015). The spindle unit can also be translated along the X- and Y-axes to machine jig blank body (1015). The positioning component or components can rotate a full 360° about the rotational axis ω of CNC machine (1000), so that various surfaces, including a top surface (1017) and a bottom surface (1018) of the jig blank body (1015), can be machined and accessed. Thus, a workable volume (1019) can be accessed at a variety of angles as the positioning component or components are rotated about rotational axis ω.

By using a CNC machine in the methods described here to automatically machine the arthroplasty jig blanks, the machining time for a custom arthroplasty jig may be reduced from about 2-3 hours to about 20 minutes or less. In addition, the use of arthroplasty jig blanks having jig blank bodies that have a size, shape, surface, and/or feature of the final desired jig or that are close to that of the final desired jig, for example the near-shape jig blanks described in U.S. patent application Ser. No. 11/656,323, which has already been incorporated by reference in its entirety, may reduce machining time further.

FIGS. 11A and 11B illustrate a variation of a method of removing the arm fixture component from a machined jig blank. As shown there, a machined jig blank (1100) has an arm fixture component (1120) and a jig blank body (1150). A machining tool such as a milling tool is applied to all attachment regions (1130a), (1130b), (1130c), and (1130d) between arm fixture component (1120) and jig blank body (1150) to remove the arm fixture component from the jig blank body, thereby forming the finished custom arthroplasty jig (1150'). Other methods may be used in some cases to remove an arm fixture component from a machined jig blank (e.g., cleaving along a prescored line). After the arm fixture component has been removed, the machined jig blank may undergo further processing (e.g., polishing and/or filing to remove burrs, etc.).

Methods are also provided for making an arthroplasty jig blank. Arthroplasty jig blanks may be formed using, for example, polymer molding or forming techniques, such as injection molding and/or compression molding.

Injection molding includes forming a mold, and injecting the mold with an injectable thermoplastic or thermosetting polymer or polymer blend. If a thermoplastic polymer or polymer blend is used, then the thermoplastic polymer or polymer blend is allowed to cool below its melt. If a thermoset polymer or polymer blend is used, then the thermoset polymer or polymer blend is allowed to cure in the mold. Thereafter, the molded polymer or polymer blend is released from the mold to form an arthroplasty jig blank comprising a jig blank body and an arm fixture component that is integral with, or coupled to, the jig blank body.

Compression molding involves filling an open mold with a thermoplastic or thermoset polymer or polymer blend, closing the mold to apply pressure to force the polymer or polymer blend to fill the mold, and then allowing a thermoplastic to cool below its melt or curing a thermoset polymer or polymer blend in the mold before releasing the mold. In many cases, with either injection molding or compression molding, the arm fixture component and the jig blank body will form a unitary body that is formed in a single mold. However, in some cases, the arm fixture component may be molded and formed separately from the jig blank body, and the two can then be affixed together as a separate step.

Because right angles may present difficulties in injection-molded pieces and in polymer molding techniques in general, the arm fixture component may be designed to contain no right angles, or few right angles. For example, and referring now to FIG. 12, the U-shaped members (1221) and (1222) of an arm fixture component (1220) of a jig blank (1200) have corners (1230) including beveled exterior surfaces (1231) and beveled interior surfaces (1232) instead of a right angle. However, the U-shaped members still have two orthogonal, planar surfaces (1233) and (1234) that can be used to align the jig blank with translational axes of the machining device. The jig blank body (1250) also may include beveled edges (1236) to facilitate molding of the jig blanks.

Any suitable polymer may used to mold or form the arthroplasty jig blanks. For example, moldable biocompatible polymers such as acetal resins, e.g., Delrin™, Nylon™ polycarbonates, polyetheretherketones (PEEK), polyethylenes, polypropylenes, Teflon™, polystyrenes, polyacrylates, polyamides, polyesters, polyurethanes, vinyl polymers, and combinations or blends thereof may be used. Additionally, more than one material may be used in forming an arthroplasty jig blank.

While the systems, methods, and devices have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the appended claims.

What is claimed is:

1. A blank from which an arthroplasty jig is to be manufactured, the blank comprising:
    a body comprising a shape and size that approximates the arthroplasty jig, the body being configured such that the entirety of the arthroplasty jig is manufactured from the body; and
    a member extending from the body and configured to support the body during manufacturing, the member being formed with the body as a unitary structure formed from a single mold.

2. The blank of claim 1, wherein the member is cantilevered off of the body.

3. The blank of claim 2, wherein the member comprises a single intersection with the body.

4. The blank of claim 3, wherein the member comprises a cylindrical shaft.

5. The blank of claim 3, wherein the member comprises a rectangular transverse cross section.

6. The blank of claim 3, wherein the member comprises a length extending away from the body, a width perpendicular to the length, and a height perpendicular to both the length and width, wherein both the width and the height are substantially smaller than the body at the single intersection.

7. The blank of claim 6, wherein the member further comprises a free end opposite the member from the single intersection, the free end comprising a structure having a length extending generally transverse to the length of the member.

8. The blank of claim 3, wherein the member comprises a length extending away from the body, a width perpendicular to the length, and a height perpendicular to both the length and width, wherein height is substantially smaller than the body at the single intersection, and the width is substantially greater than the height.

9. The blank of claim 8, wherein the member further comprises openings extending through the height.

10. The blank of claim 2, wherein the member comprises a first intersection with the body and a second intersection with the body, the first intersection and second intersection being spaced apart from each other.

11. The blank of claim 10, wherein the first intersection and second intersection being spaced apart from each other defines a first structure and a second structure of the member, the first and second structures being spaced apart from each other.

12. The blank of claim 11, wherein the first structure comprises a first length extending away from the body, a first width perpendicular to the first length, and a first height perpendicular to both the first length and first width, wherein both the first width and the first height are substantially smaller than the body at the first intersection.

13. The blank of claim 12, wherein the second structure comprises a second length extending away from the body, a second width perpendicular to the second length, and a second height perpendicular to both the second length and second width, wherein both the second width and the second height are substantially smaller than the body at the second intersection.

14. The blank of claim 13, wherein the member further comprises a free end opposite the member from the first intersection, the free end comprising a third structure having a third length extending between the first structure and second structure generally transverse to the first length.

15. The blank of claim 14, wherein the first, second and third structures combine to form a first U-shaped member.

16. The blank of claim 15, further comprising a second U-shaped member extending from an opposite side of the body from the first U-shaped member.

17. The blank of claim 14, wherein the first, second and third structures combine to form a π-shaped member.

18. The blank of claim 1, wherein the arthroplasty jig approximately by the shape and size of the body comprises a tibial arthroplasty jig.

19. The blank of claim 1, wherein the arthroplasty jig approximately by the shape and size of the body comprises a femoral arthroplasty jig.

20. The blank of claim 1, wherein the blank comprises a polymer material.

\* \* \* \* \*